(12) United States Patent
Reifenrath

(10) Patent No.: US 6,444,216 B2
(45) Date of Patent: *Sep. 3, 2002

(54) NATURAL INSECT REPELLENT

(75) Inventor: William G. Reifenrath, Novato, CA (US)

(73) Assignee: Stratacor, Inc., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/929,547

(22) Filed: Aug. 13, 2001

Related U.S. Application Data

(63) Continuation of application No. 09/107,700, filed on Jun. 30, 1998, now Pat. No. 6,306,415.
(60) Provisional application No. 60/051,320, filed on Jun. 30, 1997.

(51) Int. Cl.$^7$ .......................... A01N 25/04; A01N 37/02
(52) U.S. Cl. ...................... 424/406; 424/405; 424/407; 424/45; 424/DIG. 10; 514/558; 514/675; 514/724; 514/770; 514/919
(58) Field of Search ................................. 424/405, 406, 424/407, 45, DIG. 10; 514/919, 558, 675, 724, 770

(56) References Cited

U.S. PATENT DOCUMENTS

| | | | |
|---|---|---|---|
| 2,254,665 A | 9/1941 | Ralston et al. | |
| 3,668,226 A | 6/1972 | Quintana et al. | |
| 4,202,129 A | 5/1980 | Greenberg | |
| 4,205,086 A | 5/1980 | Babayan | |

(List continued on next page.)

FOREIGN PATENT DOCUMENTS

| | | |
|---|---|---|
| DE | 4206090 A1 | 9/1993 |
| JP | 63-48203 | 2/1988 |

OTHER PUBLICATIONS

Le Quere, et al., "Goat cheese flavor: identification of the character impact compounds", Int. Dairy Fed., 1996., 9603, (Caplus abstract 1997:195102).

W. V. King, "Chemicals Evaluated as Insecticides and Repellents at Orlando, Fla.", U.S. Department of Agriculture, Agriculture Handbook No. 69, Issued May 1954, 7 pages.

William G. Reifenrath, et al., "Evaporation and Skin Penetration Characteristics of Mosquito Repellent Formulations", Journal of the American Mosquito Control Association, vol. 5, Mar. 1989, No. 1, pp. 45–51.

(List continued on next page.)

Primary Examiner—Neil S. Levy
(74) Attorney, Agent, or Firm—Townsend, Townsend and Crew LLP

(57) ABSTRACT

A topical insect repellent with extended duration of protection was obtained from mixtures of molecules based on two or more volatile repellent organic molecular species occurring naturally on the human skin surface. The novel repellent comprises mixtures of lower, intermediate, and higher volatility organic molecules. Active ingredients for formulations are obtained from homologous series of carboxylic acids, alcohols, ketones, and lactones which span a similar range of volatility and which occur naturally on the skin surface. Volatile silicone fluid imparts mildness and water repellency to the repellent formulations. The new natural repellent exhibits the longevity and repellency that is comparable to N,N-diethyl-m-toluamide (DEET), a synthetic compound employed in almost all commercial formulations, but the inventive natural repellent is more acceptable than DEET, which has an unpleasant odor and imparts a greasy feel to the skin. The inventive insect repellent, formulated in a volatile silicone fluid, was shown to repel and incapcitate stable flies. This finding demonstrated that repellency was not limited to mosquitoes, but extends to other biting flies or insects, thus demonstrating the utility of the novel insect repellent for protecting pets and livestock as well as humans.

22 Claims, 15 Drawing Sheets

Repellency of Formulated C8910 vs Skintastic against A. aegypti

U.S. PATENT DOCUMENTS

| | | | |
|---|---|---|---|
| 4,707,496 | A | 11/1987 | Simmons |
| 4,818,535 | A | 4/1989 | Baines et al. |
| 5,064,859 | A | 11/1991 | Crammer et al. |
| 5,093,326 | A | 3/1992 | Herman |
| 5,321,048 | A | 6/1994 | Wilson et al. |
| 5,587,401 | A | 12/1996 | Vander Meer et al. |
| 5,589,181 | A | 12/1996 | Bencsits |
| 5,594,029 | A | 1/1997 | Bencsits |
| 5,695,802 | A | 12/1997 | Van Den Ouweland et al. |
| 5,855,903 | A | 1/1999 | Warren et al. |
| 6,306,415 | B1 * | 10/2001 | Reifenrath .................. 424/406 |

OTHER PUBLICATIONS

William G. Reifenrath, "Volatile Substances", Cosmetics & Toiletries, vol. 110, Jul. 1995, pp. 85–93.

W. A. Skinner, et al., "Influence of Human Skin Surface Lipids on Protection Time of Topical Mosquito Repellent", Journal of Pharmaceutical Sciences, vol. 66, No. 12, Dec. 1977, pp. 1764–1766.

W. A. Skinner, et al., "Human Skin–Surface Lipid Fatty Acids–Mosquito Repellents", Experientia, vol. 26, 1970, pp. 728–730.

W. A. Skinner, et al., "Repellency of Skin Surface Lipids of Humans to Mosquitoes", Science, 149, 1965, pp. 305–306.

W. A. Skinner, et al., "The Design of Insect Repellents", Drug Design, vol. 10, pp. 277–305 1980.

* cited by examiner

Figure 2:
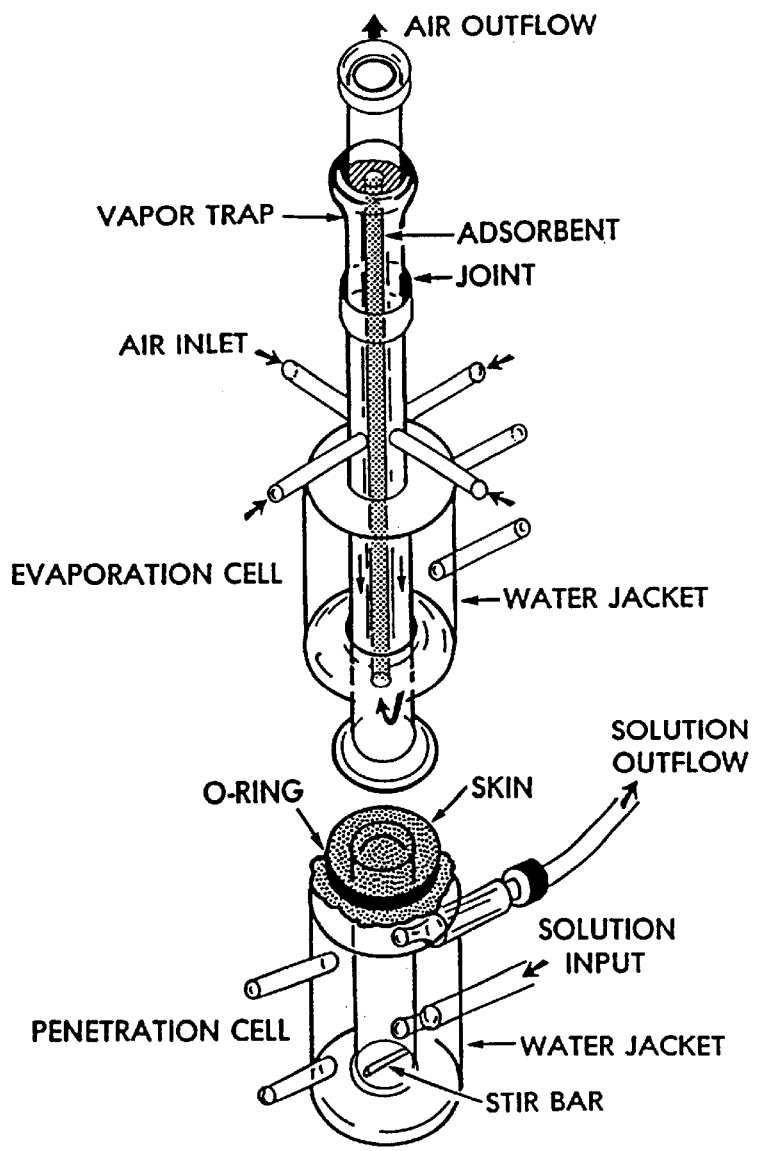

Figure 2. Apparatus for Skin Penetration/Evaporation Studies

Repellency of Compounds (0.3 mg/cm2) on Skin at T = 2 Hour

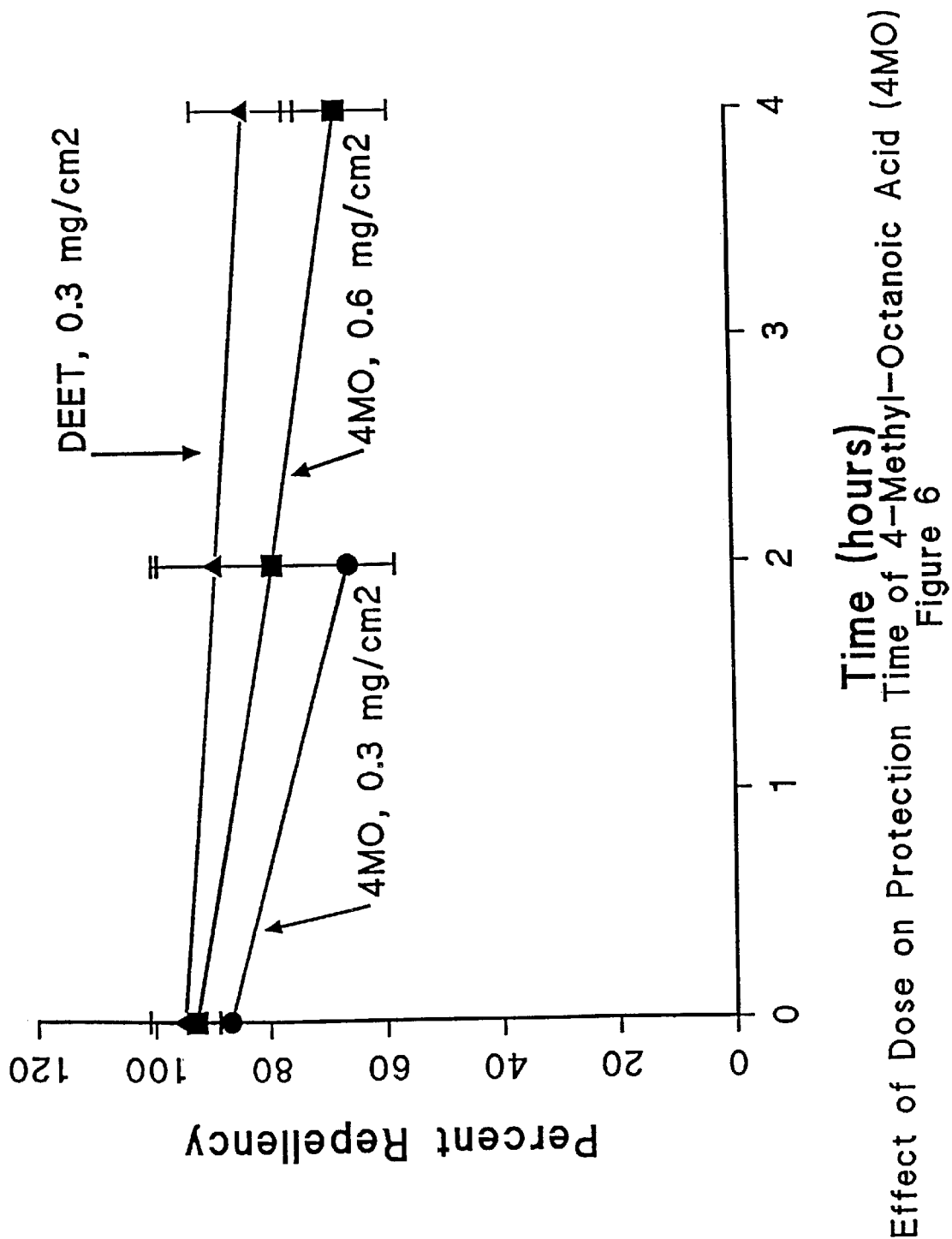

Protection Time of Individual Compounds, 0.3 mg/cm2

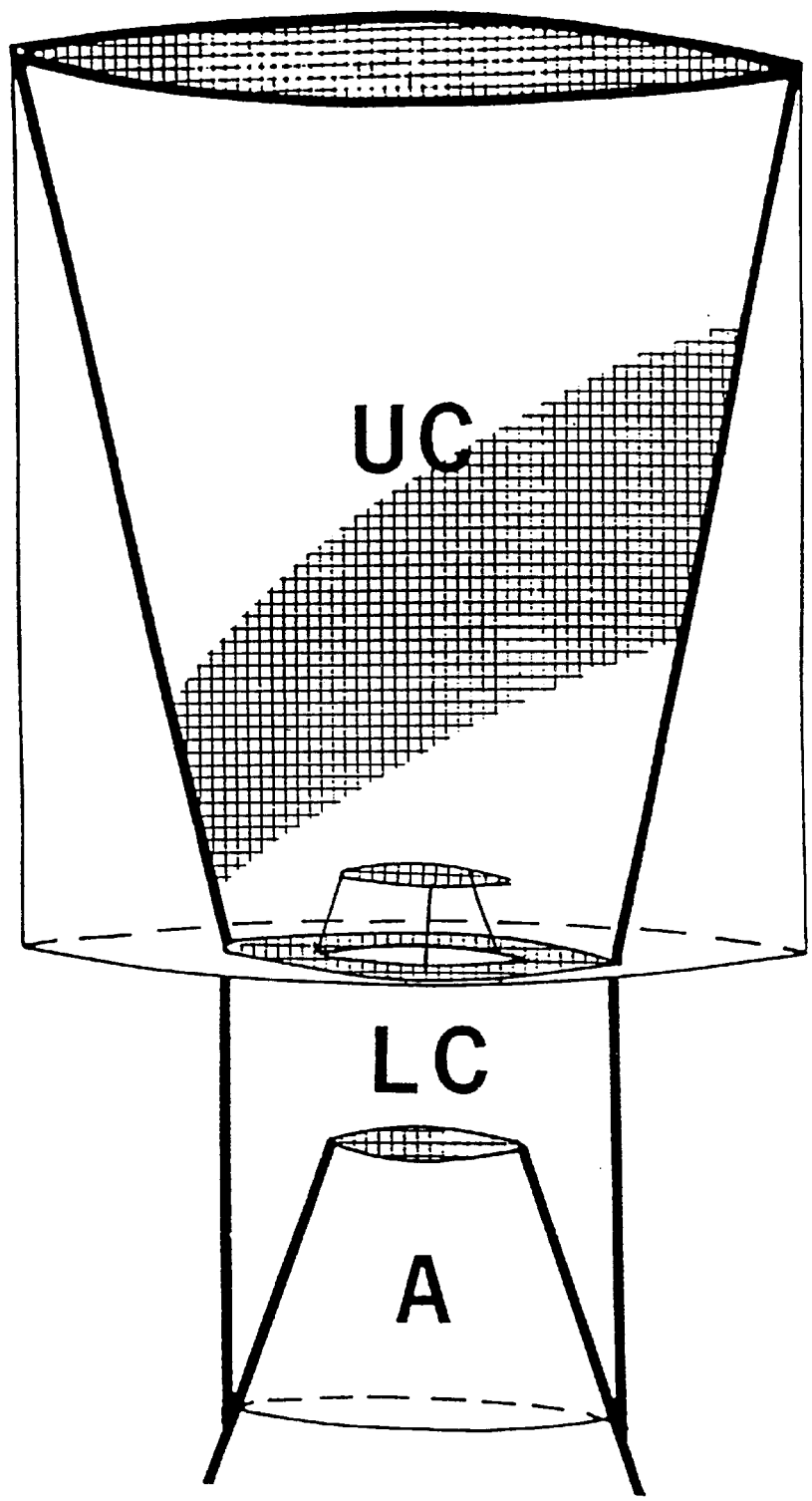
Figure 8. Modified Feinsod-Spielman Olfactometer

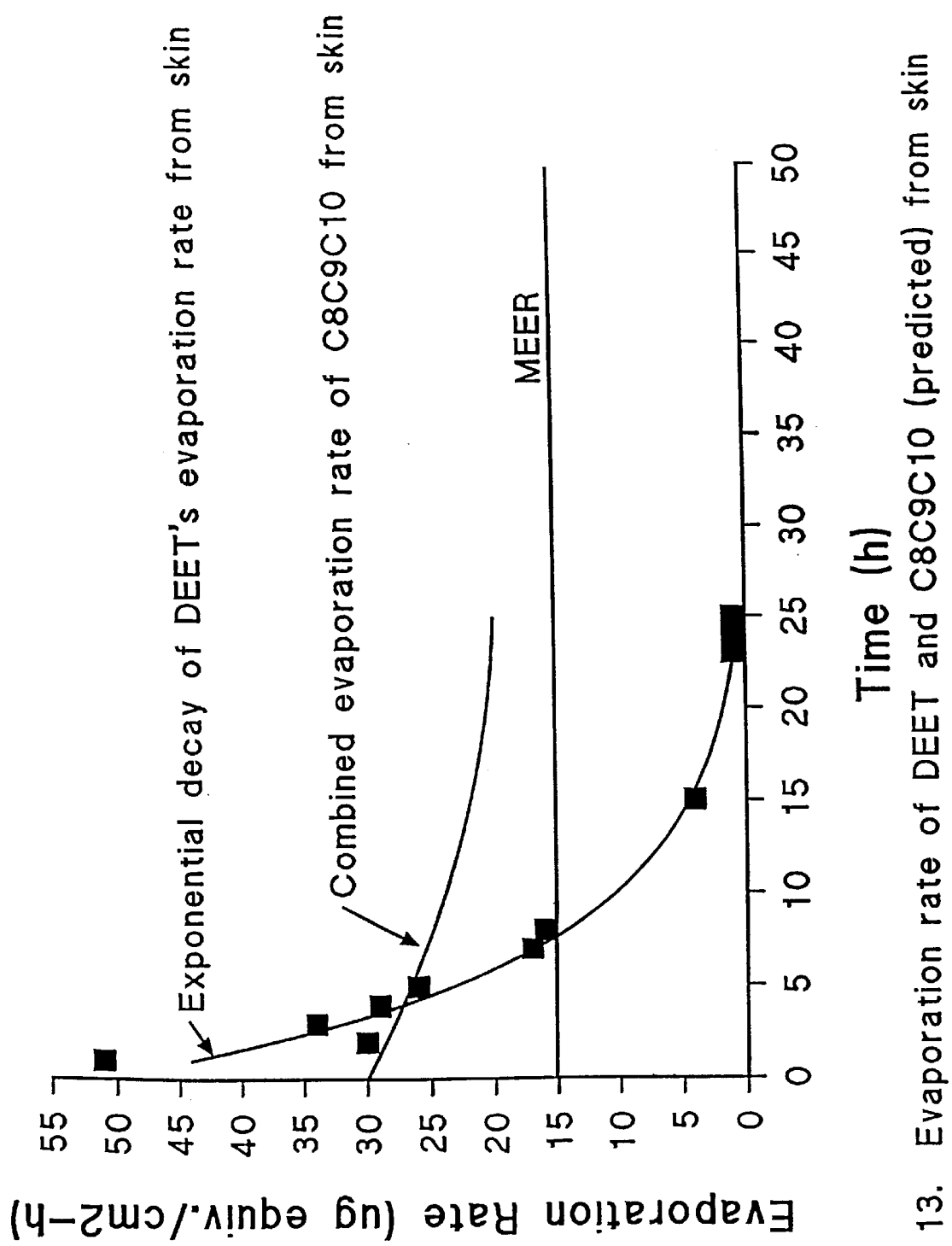
Figure 13. Evaporation rate of DEET and C8C9C10 (predicted) from skin

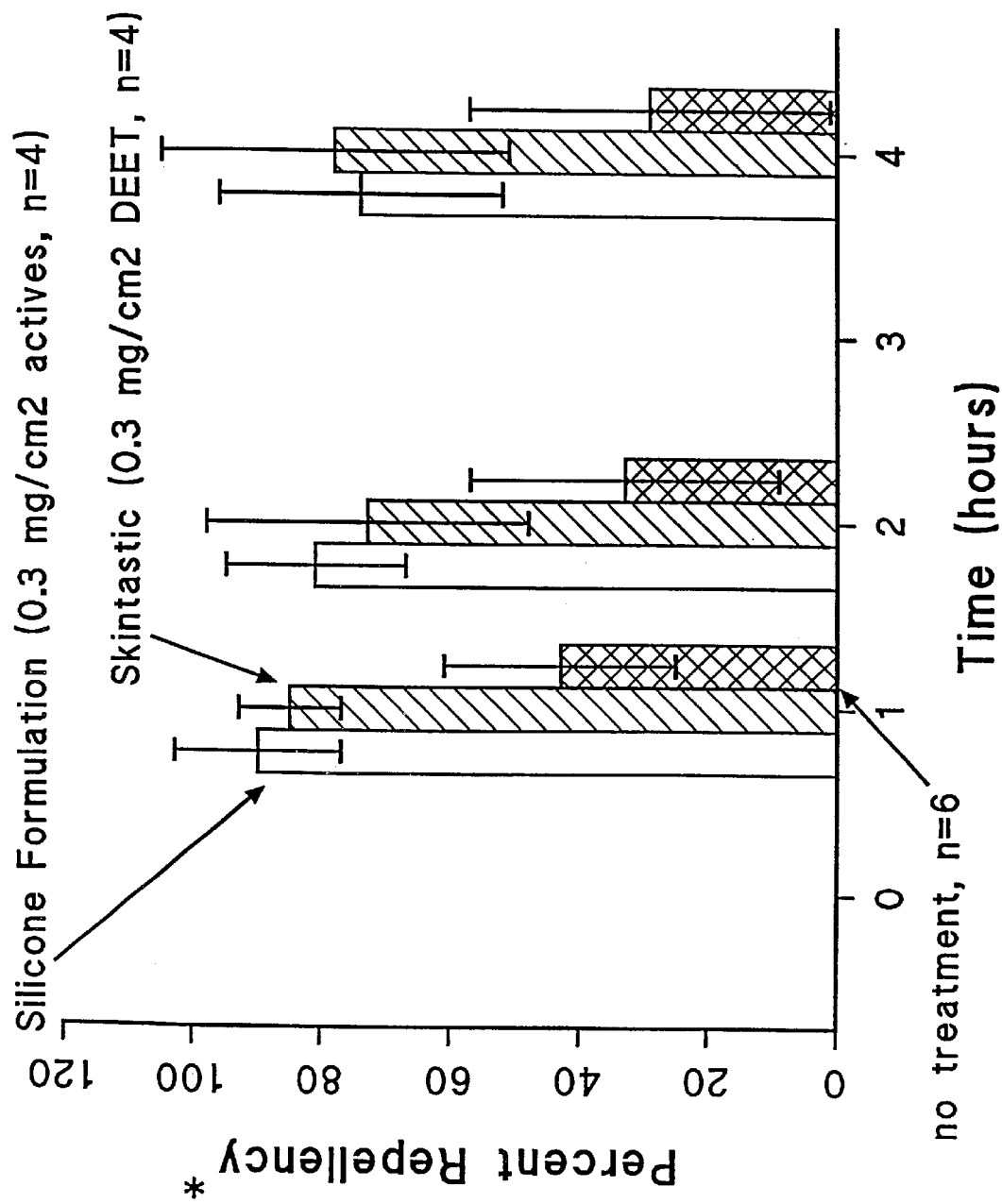
Figure 14. Repellency of Formulated C8910 vs Skintastic against A. aegypti

NATURAL INSECT REPELLENT

This application is a continuation of non-provisional U.S. patent application Ser. No. 09/107,700, filed Jun. 30, 1998, now U.S. Pat. No. 6,306,415 B 1 which is herein incorporated by reference in its entirety for all purposes. This application also claims the benefit of prior U.S. application Ser. No. 60/051,320, filed Jun. 30, 1997 and is herein incorporated by reference.

I. BACKGROUND OF THE INVENTION

1. Field of the Invention

This invention relates generally to insect and arthropod repellents and more specifically to mosquito, fly, tick and mite repellents using biologically based components.

2. Description of Related Art

At the present time, N,N,-diethyl-m-toluamide (DEET) is the active ingredient of most commercial topical insect repellents (see Table 1, below), and the current US Army insect repellent (EDTIAR) contains DEET as its active ingredient. The major commercial brands, Off!®, "Deep Woods Off!®, and Cutter®, are all DEET based products and comprise 85% of insect repellent sales (Consumer Reports Buying Guide, 1994 Special Year-End Issue). Consumer Reports tests indicated that products with the highest concentration of DEET lasted the longest against mosquitoes, but cautioned that excessive use of DEET could pose some risk, especially for children. Other disadvantages associated with DEET include: It is a synthetic chemical having a limited spectrum of activity and a noticeably unpleasant odor; DEET is a powerful plasticizer and will dissolve or mar many plastics and painted surfaces; DEET plasticizes the inert ingredients typically used in topical formulations in order to lengthen the time of effectiveness. This leads to DEET formulations with low user acceptability.

TABLE 1

Commercial Topical Insect Repellents

| Product | Manufacturer | Ingredients |
| --- | --- | --- |
| Ben's Backyard ® | Tender | DEET, 23% |
| Ben's Max ® | Tender | DEET, 95% |
| Cutter Insect Repellent ® | Miles Inc. | DEET, 21.85% |
| Muskol Maximum Strength ® | Schering-Plough | DEET, 100% |
| Muskol Ultra ® | Schering-Plough | DEET, 38% |
| Natrapel ® | Tender | Citronella oil, 10% |
| Off Deep Wood Formula ® | S. C. Johnson | DEET, 28.5% |
| Off Skintastic Insect Repellent ® | S. C. Johnson | DEET, 7.125% |
| Off Spring Fresh ® | S. C. Johnson | DEET, 14.25% |

In recent years, a proprietary bath oil (Skin-So-Soft®, Avon Products, Inc., New York) has been used as a topical insect repellent. Two of its ingredients (diisopropyl adipate and benzophenone) are repellent to *Aedes aegypti* (King, W. V. 1954. Chemicals evaluated as insecticides and repellents at Orlando, Fla. U.S. Dept. of Agriculture, Agriculture Handbook No. 69:1–397). However, the bath oil was reported as less effective and less persistent than DEET (Rutledge et al., 1982, *Repellent activity of a proprietary bath oil* (Skin-So-Soft), Mosquito News:42:557–559).

Efforts to develop a natural insect repellent have motivated studies of oils of citronella, turpentine, pennyroyal, cedarwood, eucalyptus and wintergreen, but these are relatively ineffective (Handbook of Nonprescription Drugs, 1993, 10th Ed., American Pharmaceutical Assn., Washington, D.C.). Consumer Reports tests indicated that "natural products" and products without DEET, including Skin-So-Soft®, provided little or no protection against mosquitoes (Consumer Reports Buying Guide, 1994 Special Year-End Issue). Insect repellents for nonprescription oral use are not generally recognized as safe and effective (Federal Register, 1985, 50:25170).

Franz Bencsits describes "Use of First Runnings Coconut Fatty Acid as Insect-repellent" in U.S. Pat. No. 5,594,029. Although Bencsits does not describe specifically what "first runnings" of coconut fatty acids are, he describes that combining the "first runnings" with ". . . another active substance, an oil or fat selected from the group consisting of rape-seed oil, sunflower oil, peanut oil/butter, . . . " etc. provides an insect repellent. Because the term "first runnings" is not a term of art and is not understood by the average knowledgeable person working in the field, it is impossible to know exactly what substance Bencsits tested. The average knowledgeable person working in the field of formulating insect repellents does not know what "first runnings" are or how to obtain them. Many experts also do not understand this term and were not able to discover its meaning even with research. Furthermore, the limited number of tests and controls, and lack of attention to fatty acids as potential skin irritants appear to limit Bencsits' invention to non-animal surfaces.

Bencsits teaches the use of up to 15% potassium hydroxide (KOH) in his formulations. KOH ionizes fatty acids, turning them into non-volatile salts. Bencsits thus teaches away from the utility of volatile compounds.

Bernard Crammer, et al. Describes in U.S. Pat. No. 5,064,859, a method for killing lice and lice eggs that have infested human skin and hair with a $C_8$ to $C_{12}$ alkyl radical. The patent does not mention repelling live approaching insects.

Stephen Herman describes, in U.S. Pat. No. 5,093,326, a composition comprising an ozonized derivative of unsaturated hydrocarbon for repelling insects from a surface. Performance does not appear competitive with DEET.

Clearly there is a need for a long-lasting effective insect repellent that is pleasant to use and that will not damage plastic containers, or the text printed on the containers.

II. SUMMARY OF THE INVENTION

It is an object of the present invention to provide an insect and arthropod repellent that is safe, long-lasting, effective and pleasant. It is a further object for the inventive formulation to avoid the damage to plastic containers and the text printed on the containers that is associated with currently effective insect repellent formulations.

The present inventive insect and arthropod repellent comprises a combination of two or more homologous volatile repellent molecules, similar or identical to those normally found on human skin, wherein at least one of the molecules has a vapor pressure between about 0.1 mm Hg and about 10 mm Hg at 125° C. and at least one other molecule has a vapor pressure between about 5 mm Hg and about 100 mm Hg at 125° C.

III. SUMMARY DESCRIPTION OF THE DRAWINGS

Figure 1:
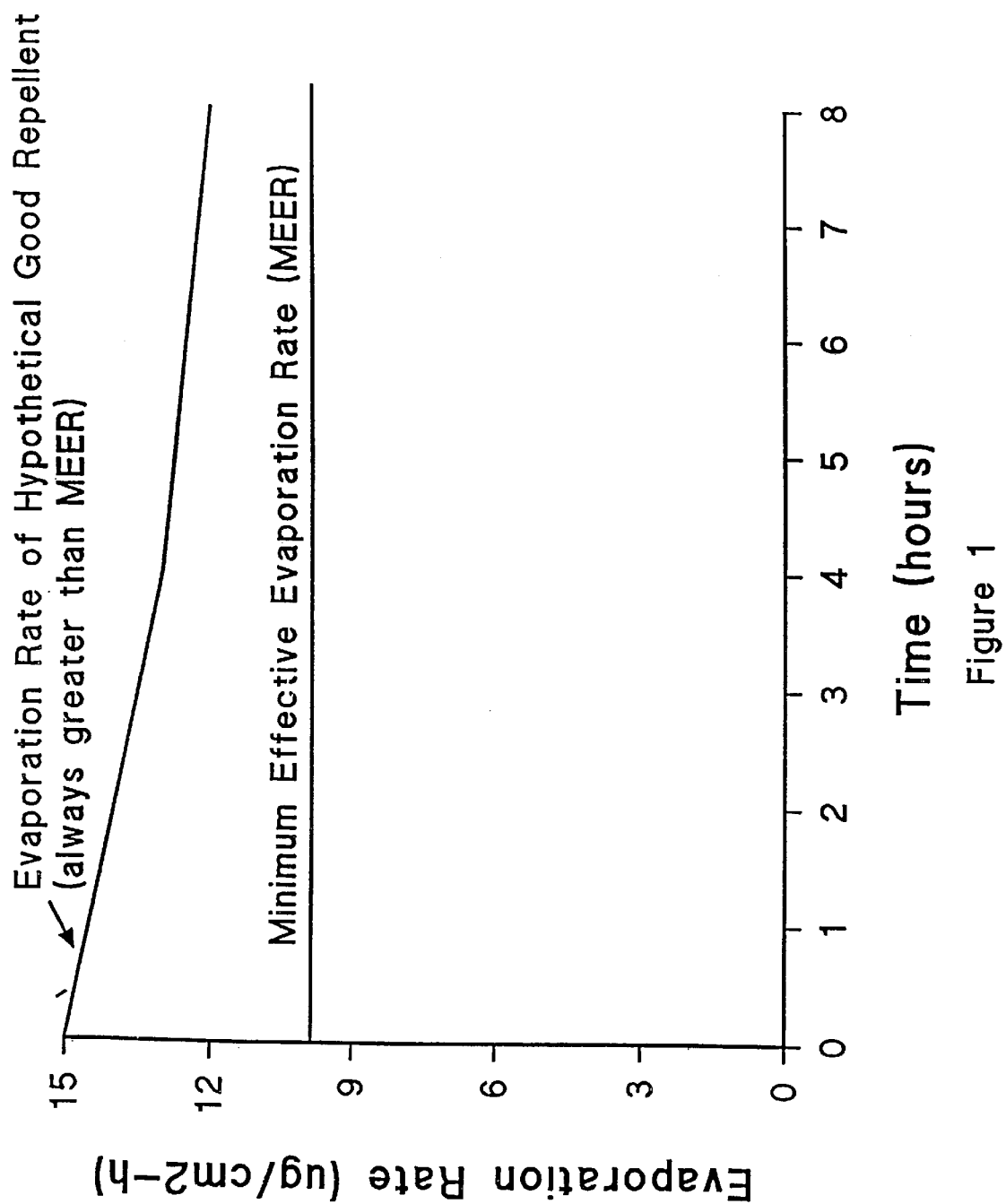

FIG. 1: illustrates the evaporation rate of such a hypothetical long-lasting repellent having a relatively constant evaporation rate sufficiently above the MEER to maintain effective repellency.

FIG. 2: shows schematic diagram of a Skin Penetration/Evaporation laboratory apparatus.

Figure 3:
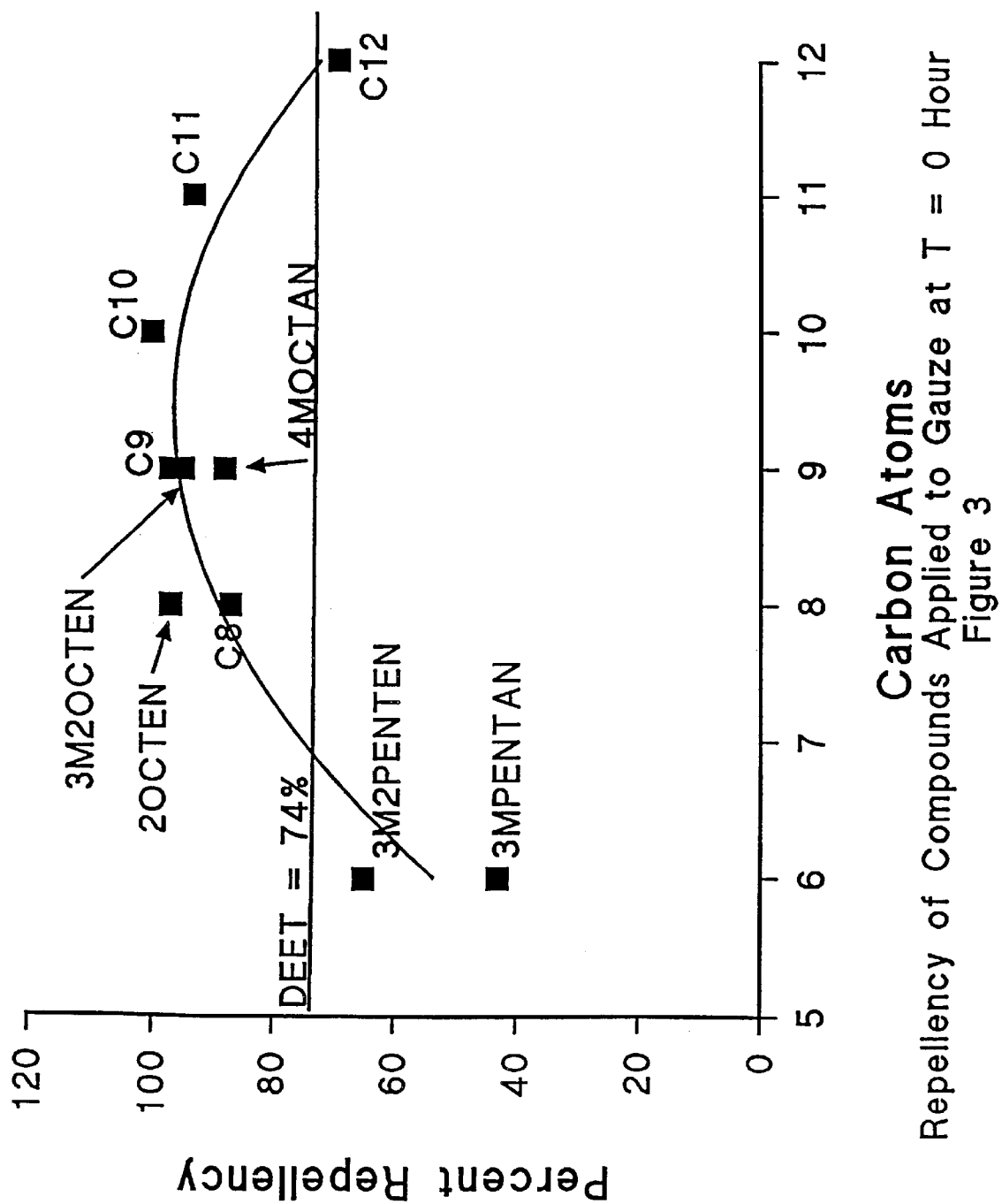

FIG. 3: shows the percent repellency of homologs containing 8 to 11 carbon atoms applied to gauze, compared to DEET.

Figure 4:
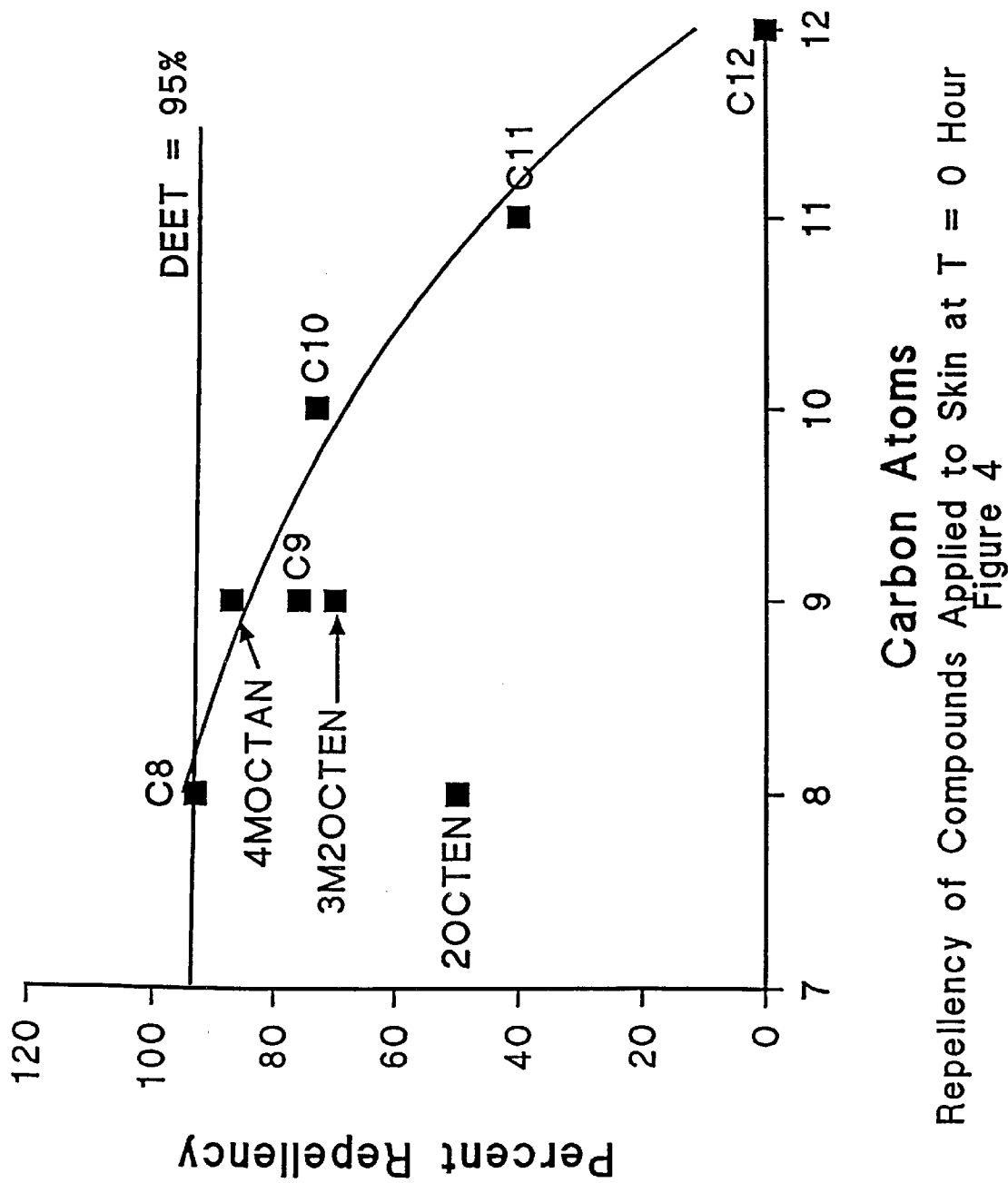

FIG. 4: shows the percent repellency of homologs containing 8 to 11 carbon atoms applied to skin, compared to DEET. The repellency dropped dramatically with increasing numbers of carbon atoms.

Figure 5:
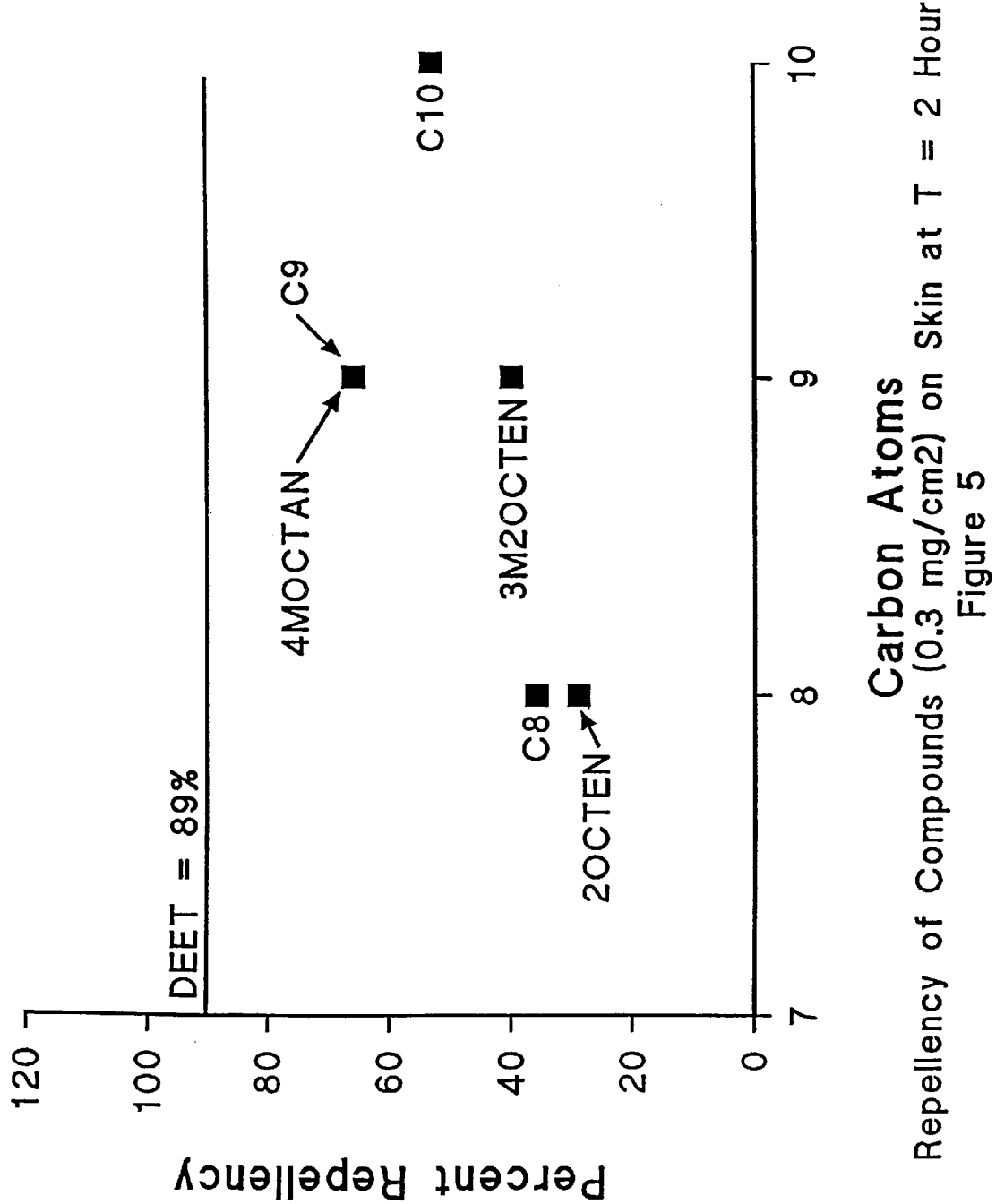

FIG. 5: shows a graph of percent repellency two hours after skin application. 4-methyloctanoic acid (4MOCTAN) and nonanoic acid (C9) had the highest repellency.

FIG. 6: shows a graph comparing the percent repellency of 0.3 and 0.6 mg/cm$^2$ 4MOCTAN and 0.3 mg/cm$^2$ DEET over a 4 hour period. Taking into consideration that about 50% of the 4MOCTAN ionizes at skin pH, the repellency of 4MOCTAN is nearly equal to that of DEET.

Figure 7A:
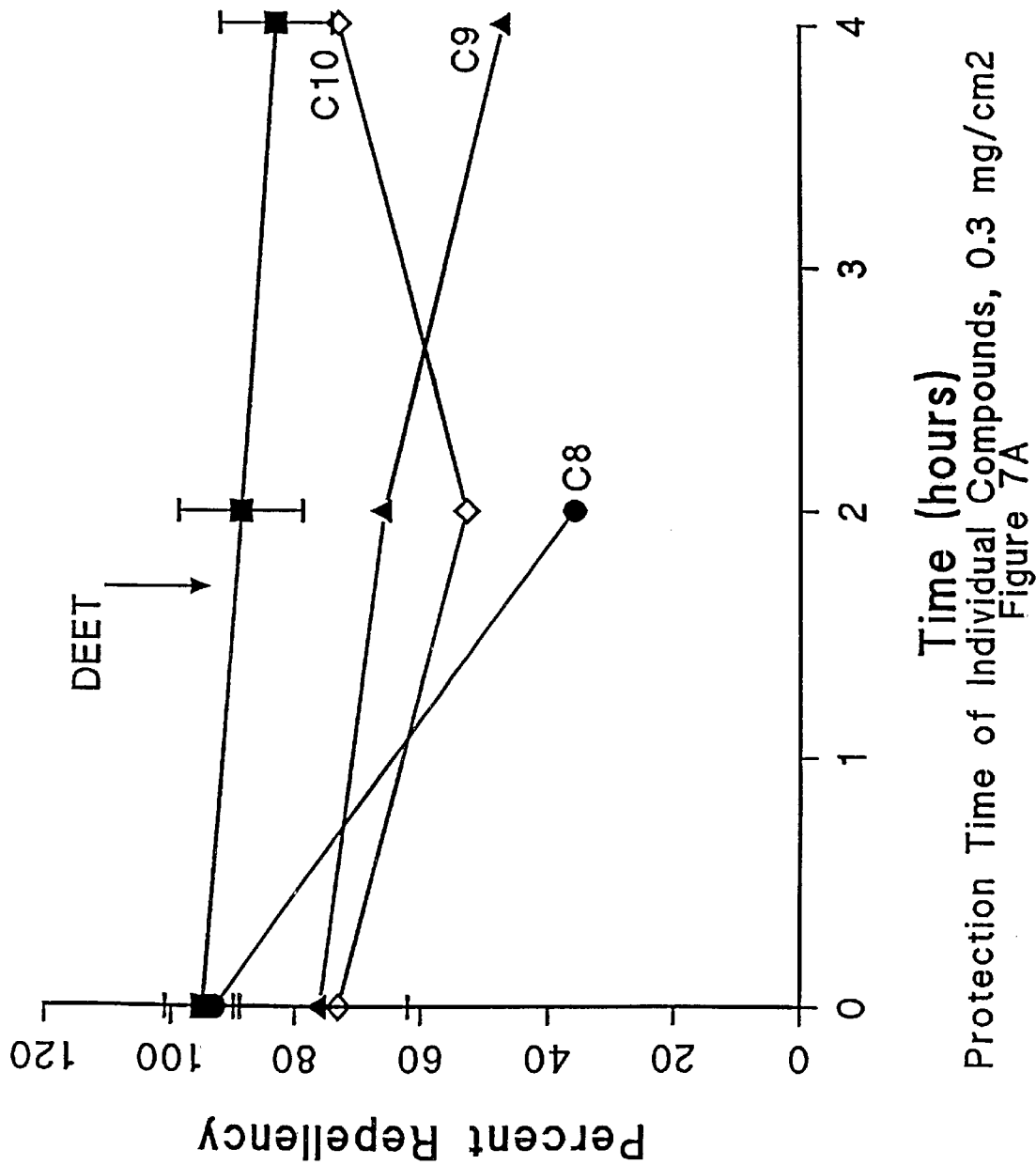

FIG. 7a: shows a graph of percent repellency vs. time for each of the three molecules, octanoic acid C8, nonanoic acid C9, and decanoic acid C10 compared to DEET.

Figure 7B:
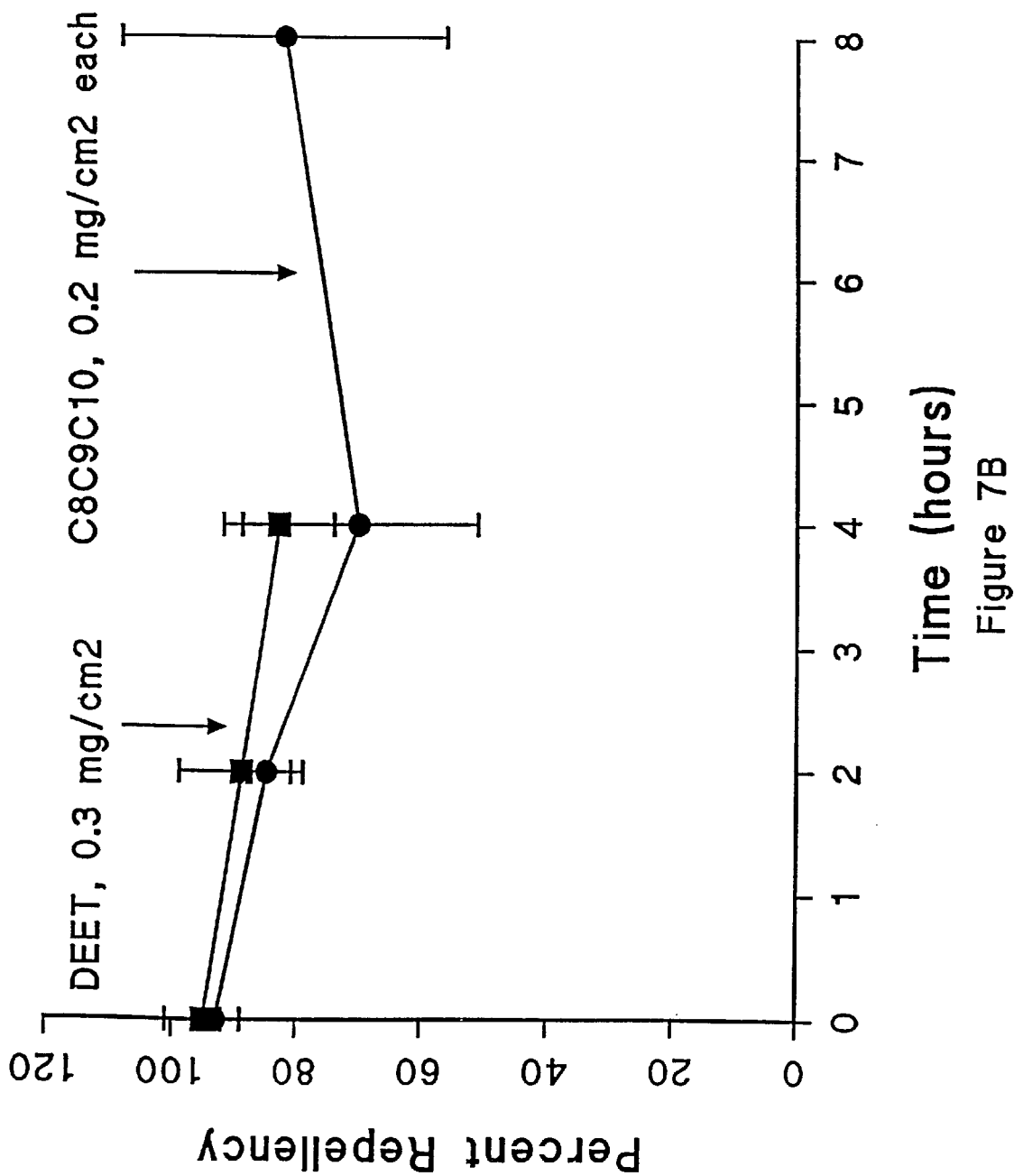

FIG. 7b: shows a graph of percent repellency vs. time for a 1:1:1 mixture of octanoic acid (C8), nonanoic acid (C9), and decanoic acid (C10), each at a topical dose of 0.2 mg/cm$^2$, and 0.3 mg/cm$^2$ DEET. The C8C9C10 combination gave repellency at 8 hours after application comparable to that of DEET at 4 hours.

FIG. 8: shows a diagram of a modified Feinsod-Spielman olfactometer.

Figure 9:
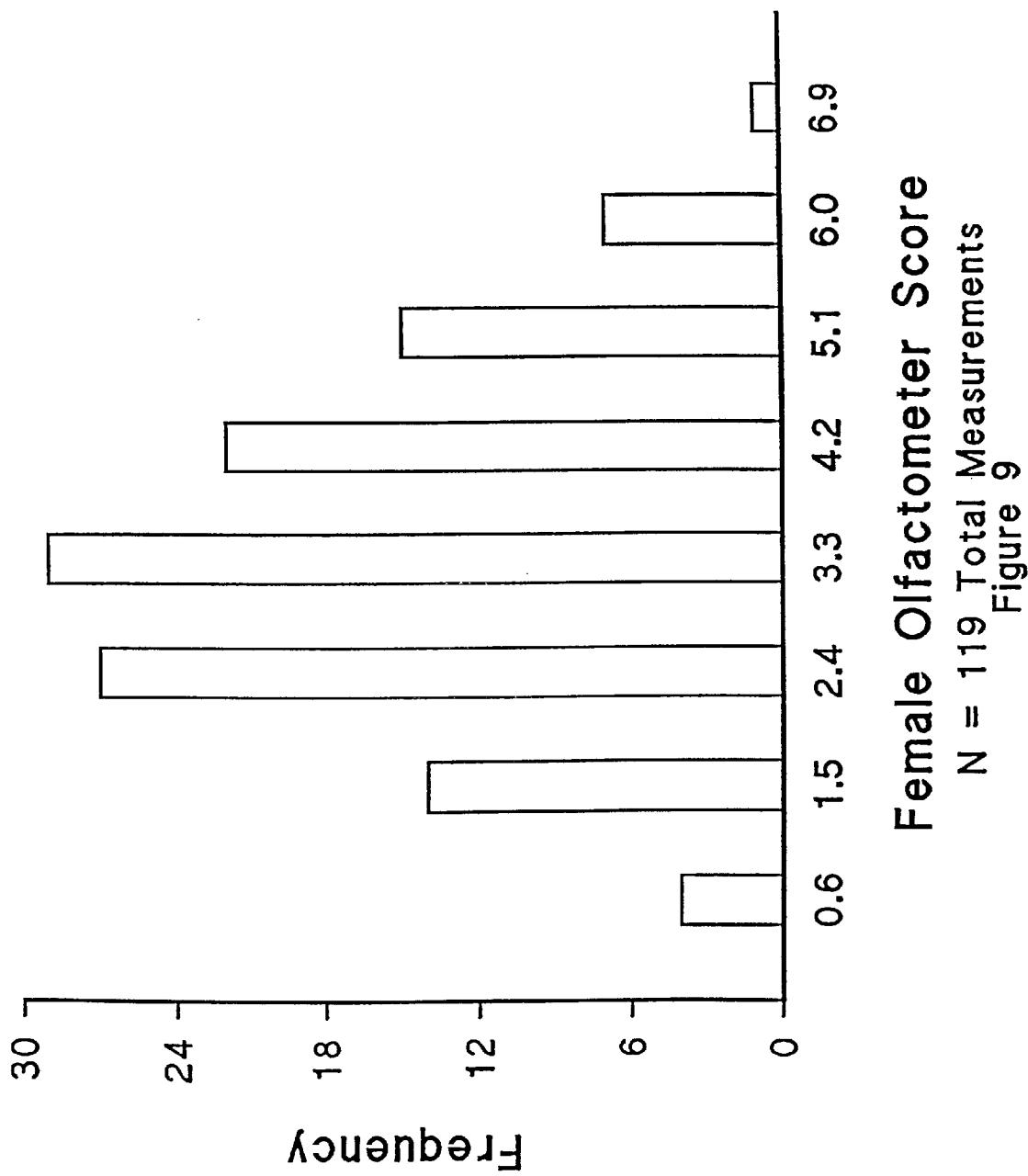

FIG. 9: shows a histogram of olfactometer scores, which measure attractancy of female test subjects. A higher number designates greater attractancy.

Figure 10:
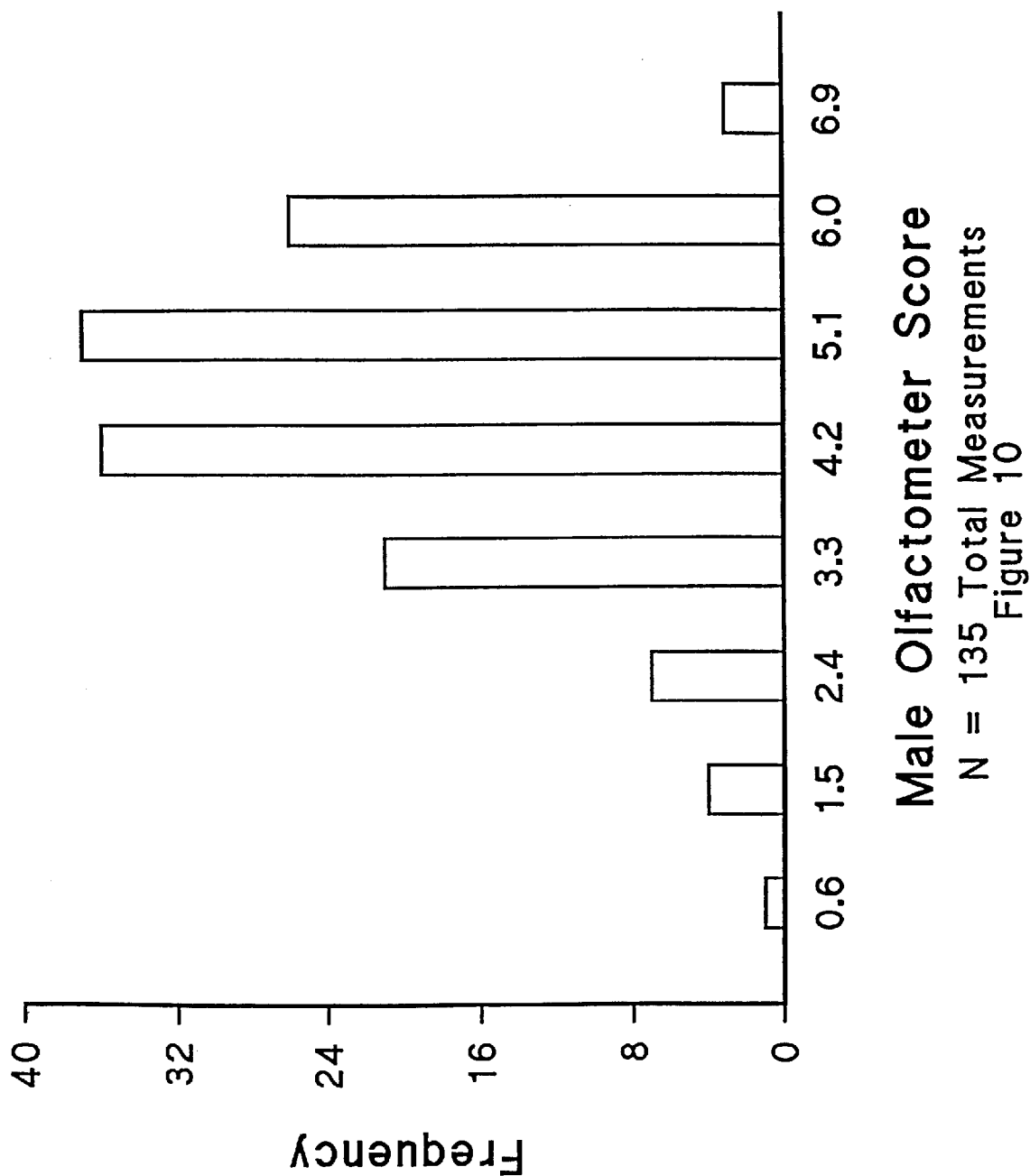

FIG. 10: shows a histogram of olfactometer scores, which measure attractancy of male test subjects. A higher number designates greater attractancy.

Figure 11:
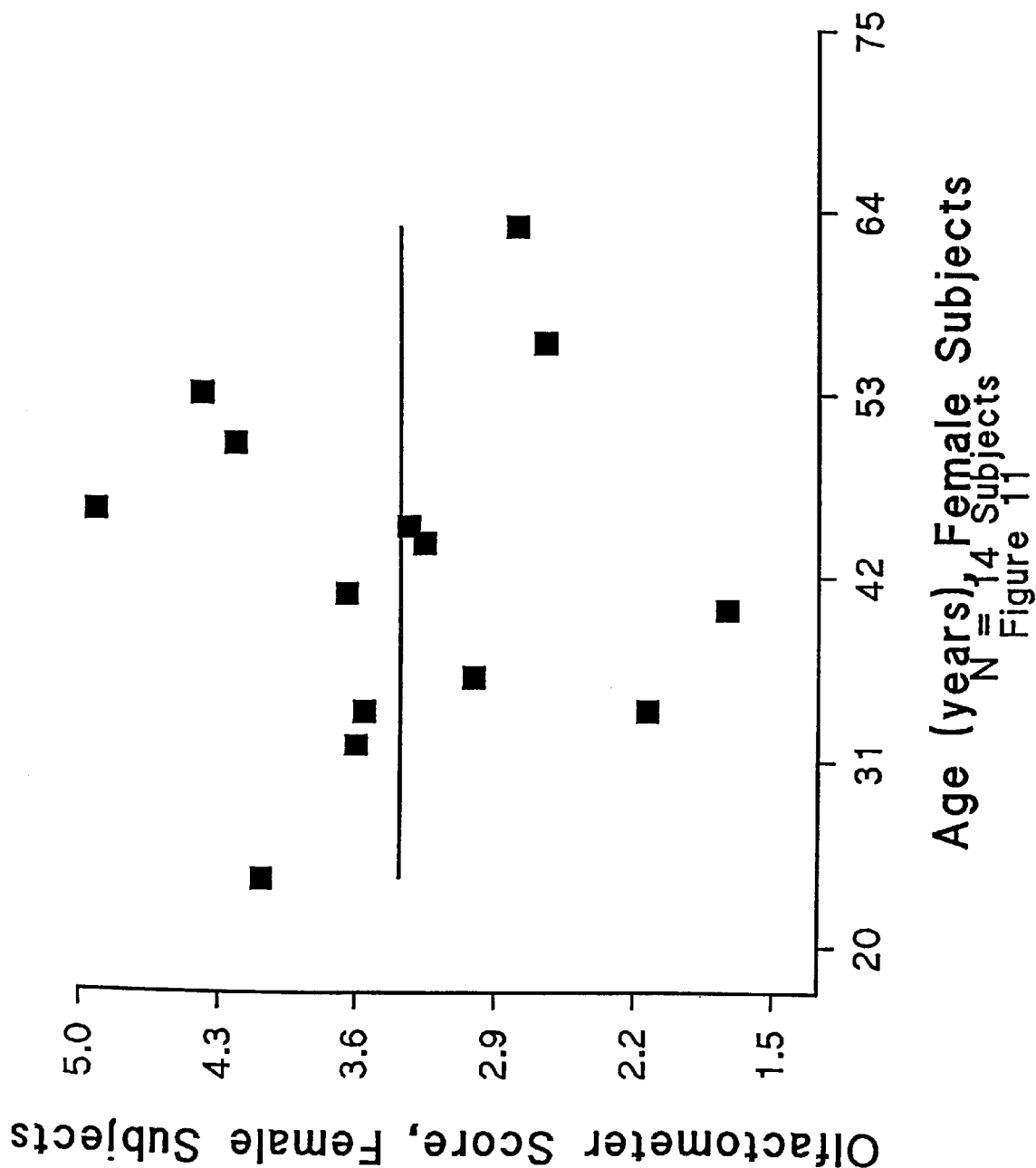

FIG. 11: shows a plot of female test subject olfactometer scores, which measure attractancy, vs. age.

Figure 12:
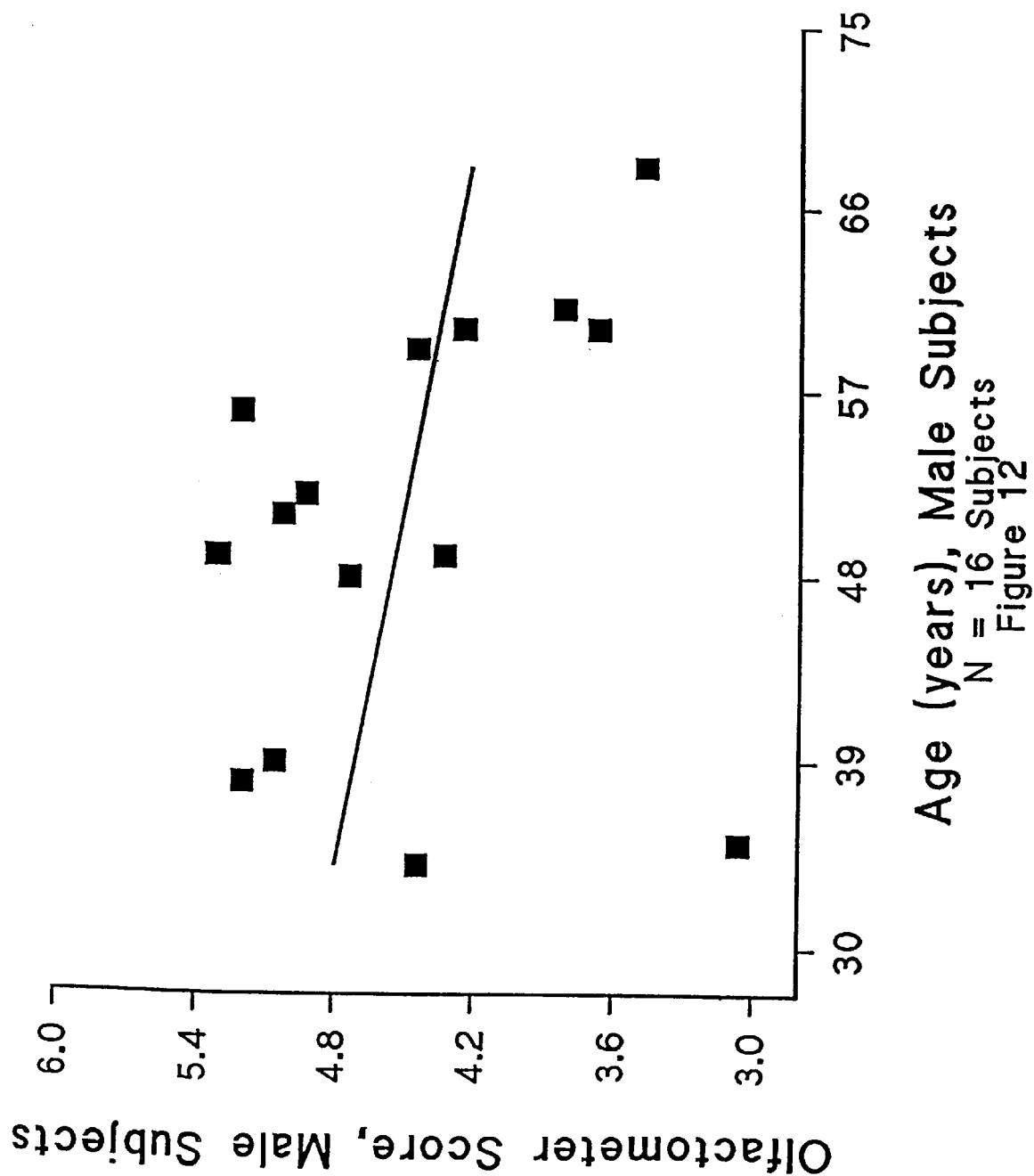

FIG. 12: shows a plot of male test subject olfactometer scores, which measure attractancy, vs. age.

FIG. 13: shows the change in evaporation rate of DEET over time, and of a mixture of equal concentrations of $C_8$, $C_9$, and $C_{10}$; the straight line represents the minimum effective evaporation rate for DEET.

FIG. 14: shows a comparison of the repellency of formulated C8C9C10 vs Skintastic against Aedes aegypti mosquitoes.

IV. DETAILED DESCRIPTION OF THE INVENTION

The present invention comprises an inventive formulation for application to skin that has a natural pleasant feel, which is made from fatty acids or other organic molecular species normally found on many people's skin, and which is approximately as effective as DEET both in terms of repellency and duration of effect. The active repellent molecules have a polar group attached to a non-polar group comprising between about three and about twelve carbon atoms. The non-polar group may comprise a branched carbon chain or an unbranched carbon chain. The polar group may comprise carboxyl, alcohol, ketone, lactone or other polar groups. An effective formulation or composition or repellent molecules comprises molecules having at least two different volatilities. To achieve such a mixture, homologous molecules having different lengths unbranched carbon chains can be used because shorter unbranched carbon chains are more volatile than longer unbranched carbon chains. Another method of achieving a mixture of volatilities is to mix homologous molecules having a branched non-polar chain with molecules having different (or no) branching configurations of the same number of carbons. It will be obvious to chemists of ordinary skill that a mixture comprising various other combinations of homologs and isomers of an active repellent molecule will result in a combination of volatilities.

The inventive formulation comprises a combination of two or more homologous volatile repellent molecules, similar or identical to those normally found on human skin, wherein at least one of the molecules has a vapor pressure between about 0.1 mm Hg and about 10 mm Hg at 125° C. and at least one other molecule has a vapor pressure between about 5 mm Hg and about 100 mm Hg at 125° C. Preferably the molecules are free fatty acid carbon chains having between 3 and 12 carbon atoms and a polar group on one end.

Preferably the repellant molecules are mixed in a dermatologically acceptable carrier. The carrier allows the formulation to be adjusted to an effective concentration of repellant molecules. The carrier may further provide water repellency, prevent skin irritation, and/or soothe and condition skin. For example the carrier may include silicone, petrolatum, lanolin or many of several other well know carrier components.

Insect repellents form an unusual class of compounds where evaporation of the active ingredient from the skin surface is necessary for effectiveness. An evaporation rate greater than the minimum effective evaporation rate (MEER) results in a significant and undesirable mode of loss. Penetration into and through the skin is also an undesirable mode of loss of compound from the skin surface. In the past, researchers attempted to balance these properties by finding a single active ingredient having the right balance of physical properties. Alternatively, the active ingredient was formulated with polymers and inert ingredients added to the active ingredient for the purpose of modifying the persistence of the active ingredient on the skin surface. Adding inert ingredients to the active ingredient limits the number of molecules of active ingredient on the surface of the repellent film. Since a molecule must be on the surface in order to evaporate, the evaporation rate is lowered. This carries with it the negative consequence of diluting the concentration of active ingredient that can be applied to the skin which in turn reduces the overall potency of a formulation containing inert ingredients. In another alternative, the active ingredient was contained in microcapsules to control rates of loss from the skin surface. Another technique of limiting the evaporation rate of active ingredient was to synthesize a precursor molecule, which slowly disintegrated on the skin surface to release the active ingredient.

Desirable properties of a topical insect repellent include low toxicity, resistance to loss by water immersion or sweating, low or no odor or at least a pleasant odor, ease of application, and rapid formation of a dry tack-free surface film. Attempts to improve the properties of DEET through polymer or microcapsule formulation have been frustrated by DEET's plasticizing properties, which lead to a high tack skin surface.

The present invention makes use of a novel method of developing a an optimal topical repellent, firstly by deriving the active ingredients from chemicals already naturally found on the skin and secondly, by using homologs of the active ingredient to optimize evaporation rate. Since the homologs also possess repellent activity, as opposed to inert ingredients which do not, the amount of active repellent on the skin surface is maximized.

When formulating the insect repellent composition it is important to combine a volume repellent molecules having relatively high volatilities with a volume of repellent molecules having a lower volatility which will remain on the skin longer. One way to achieve a mixture of volatilities is to mix organic molecules having unbranched chains of differing chain lengths, that is mixing shorter carbon chains which are more volatile with longer carbon chains. Preferably the shorter chains have between about 6 and about 8 carbon atoms per molecule. Preferably the longer chains have between about 9 and about 12 carbon atoms per molecule.

A wide variety of compounds possess insect repellent and/or mosquito repellent activity, as evidenced by the diversity of chemical structures reported by the USDA (Chemicals Evaluated as Insecticides and Repellents at Orlando, Fla., compiled by W. V. King, US Department of Agriculture, Agricultural Research Service, Agriculture Handbook No. 69) to contain repellent activity. Activity is found in alcohols, amides, esters, ketones, acids, lactones, lactams etc., and positional isomers of DEET or the diasterioisomers of ethyl hexanediol, both well studied repellents, have similar repellent activity. Activity does appear to depend on the physical properties of these compounds. One property that is important is surface activity, as most, if not all, repellents contain both polar and non-polar regions in their structure. A second property is volatility. Because mosquitoes' sensory receptors for mosquito repellents such as DEET are located on the mosquito antenna, effectiveness of a repellent compound depends on it's volatility from the skin surface. It is desirable for the repellent compound to reach the mosquito antenna before the mosquito lands on the skin. When mosquitoes' antenna are removed, they are not repelled by DEET. Many years of observations of mosquito behavior reveal that biting occurs shortly after mosquitoes begin to land on repellent treated skin.

Therefore, the evaporation rate of repellents from the skin surface is an extremely important factor in the ability of repellents to protect the skin from bites. A certain minimum concentration of repellent is needed in the air space directly above the skin surface in order to repel insects, and this concentration is a measure of the potency of the repellent. To maintain this concentration, each repellent must have a minimum effective evaporation rate (MEER) from the skin surface. The MEER will change as a function of conditions in the field. For example, as the avidity or biting tendency of a mosquito increases, a higher MEER will be required. Another important factor that influences the MEER is the concentration of mosquitoes. For example, in an environment having a low concentration of mosquitoes where those mosquitoes were not hungry, the MEER could be as low as 2, or more commonly 5, or 6. In an environment having a high concentration of hungry mosquitoes the MEER might be as high as 12 or even 15. In many environments, a MEER of about 9 or 10 is required, as indicated in FIG. 1.

The evaporation rate of a compound from the surface of the pure liquid will be a function of its vapor pressure (VP) and molecular weight (M), as given by equation (1), where f is a constant (W. F. Spencer and W. J. Farmer, Assessment of the Vapor Behavior of Toxic Organic Chemicals, in Dynamics, Exposure and Hazard Assessment of Toxic Chemicals, R Haque, ed, Ann Arbor (1980), pp. 143–161).

$$\text{Evaporation rate (bulk liquid)} = f(VP)(M)^{0.5} \tag{1}$$

When a repellent is applied in small doses to the skin surface, the evaporation rate is determined by many factors, including the rate of skin absorption. The evaporation rate will decrease with time (t) in proportion to the amount of chemical remaining on the skin surface and can be approximated by equation (2), where A is the evaporation rate at t=0 and e and k are constants.

$$\text{Evaporation rate (skin surface)} = Ae^{-kt} \tag{2}$$

At a certain time point ($t_d$) after topical application, the evaporation rate of a repellent from skin becomes less than the MEER and biting will occur. The time $t_d$ represents the effective duration of repellent protection. A long lasting repellent for the skin would have an a relatively constant evaporation rate (a low value of "k" in equation 2) that is sufficiently above the MEER. FIG. 1 illustrates the evaporation rate of such a hypothetical repellent. The insect repellent DEET was the result of an intensive search by the USDA to find such a compound. Unfortunately though, DEET repellency varies with its evaporation rate, which can be different in a laboratory instrument such as the "Skin Penetration/Evaporation Apparatus" shown in FIG. 2 and in real field conditions. Measured with the apparatus shown in FIG. 2, DEET's evaporation rate immediately after application is much higher than the MEER; the rate decreases rapidly thereafter. Under laboratory conditions DEET provides only 5–7 hours of protection and much less than that under summer field conditions.

Many attempts have been made to formulate DEET with inert ingredients to reduce its initially excessive rate of evaporative and to extend the time interval when the evaporation rate is above the MEER. However, DEET plasticizes or partially dissolves many of these materials, rendering them ineffective or creating a sticky formulation unacceptable for use on the skin. This approach also suffers from the fact that only a certain total amount of repellent formulation can be applied to the skin surface and that the addition of inert ingredients to the formulation decreases the amount of active that can be applied. Generally, the ratio (by weight) of added inert ingredient to DEET must be at least 3–4 before the additive begins to significantly affect DEET's evaporation rate (Evaporation and Skin Penetration Characteristics of Mosquito Repellent Formulations, W. G. Reifenrath, G. S. Hawkins and M. S. Kurtz, J. Am. Mosq. Control Assn., 5:45–51, 1989).

Naturally occurring fatty acids contain both polar (carboxylic acid group) and non-polar (alkyl chain) regions in their structure and the lower molecular weight homologs are sufficiently volatile to evaporate from the skin surface. Individually, these compounds have repellent activity. A number of these compounds were applied to non-absorptive gauze mounted between the human forearm and the olfactometer containing mosquitoes. These tests were done immediately after application to minimize losses due to evaporation (described fully in "Example 2" below). Because skin absorption and evaporative loss is minimized, this test can be regarded as a measure of the potency of the compounds. Homologs containing 8 to 11 carbon atoms had similar potency (percent repellency), which was greater than that of DEET (FIG. 3). Six carbon homologs and twelve carbon homologs had potency equal to or less than DEET.

These results focused attention on carboxylic acids containing six to twelve carbon atoms. When the repellency of compounds within this range was determined immediately after application to skin (described in Example 2, below), only the saturated derivatives octanoic acid (C8) and 4-methyloctanoic acid (4MOCTAN) had repellency comparable to DEET and the unsaturated derivatives 2-octenoic acid (2OCTEN) and 3-methyl-2-octenoic acid (3M2OCTEN) were less repellent (FIG. 4). Percent repellency dropped dramatically with increasing numbers of carbon atoms in the molecule (FIG. 4). Two hours after skin 2 application, 4-methyloctanoic acid (4MOCTAN) and nonanoic acid (C9) had the highest repellency (FIG. 5). The nonanoic acid was preferably saturated. 4MOCTAN had the best overall performance at the zero and two hour time points. It should be noted for FIGS. 4 and 5 that the carboxylic acids exist on the skin at a pH which ionizes 50% of the molecules (pH=pKa of the acids). Since the ionized species are not volatile, the actual available dose is approximately 50% of that for DEET. Taking this factor into consideration, the repellency of 4MOCTAN at 0.6 mg/cm$^2$ is nearly equal to that of DEET over a 4 hour period (FIG. 6). However, 4MOCTAN is thermally unstable and is not generally available commercially.

Rather than conduct a time-intensive search for a single carboxylic acid with optimal repellent properties and user acceptability (many short chain fatty acids have very strong, objectionable odors), a mixture of repellent fatty acids spanning a range of volatility was investigated. In theory, molecules in a mixture "compete" with each other for evaporative loss from the skin surface, and the initial evaporation rate of each component will be lower than that of an equal dose of pure component. Initially, each component would be expected to undergo approximately the same percentage reduction in evaporation rate if the components are present in equal amounts. The component with the highest vapor pressure will have the greatest reduction in component mass entering the air space over the skin. At later time points, the evaporation rate of each component will be higher than that of an equal dose of pure component. Again, the component with the highest vapor pressure will have the greatest increase in component mass entering the air space over the skin. Mixing less volatile, but still active, longer chains with the more volatile shorter chains, results in a constant evaporation of active repellent molecules from the surface of the film of the inventive insect and arthropod repellent after it is applied to the skin, hair or clothing of the user. The net result of the mixture will be reduction in the initial excessive evaporation of the most volatile repellent component and, at longer time points, a higher total rate of evaporation of repellent molecules into the air space over the skin. Such a result will lead to a composition with extended duration of protection. Specifically, we found that a 1:1:1 mixture of octanoic acid (C8), nonanoic acid (C9), and decanoic acid (C10), each at a topical dose of 0.2 mg/cm$^2$, was found to give repellency at 8 hours after application comparable to that of DEET at 4 hours. FIG. 7A shows the percent repellency of each component by itself, and FIG. 7B shows the percent repellency of the inventive repellent combining two or more molecules having different volatilities. An additional advantage of this mixture is the ability to easily change the ratio of components to suit conditions. If mosquito avidity or biting pressure is very high (the Florida everglades, for example), the mixture may fail immediately because the initial evaporation rate does not exceed the MEER. In this case, the proportion of C8, the most volatile component, could be increased to provide effective repellency, although some loss of duration would be expected.

The relative concentrations of molecules having more and less volatility used in a particular formulation can vary greatly depending on the needs of the user. Where it is easy to reapply repellent, a higher percent of the shorter, more volatile molecules is used; where it is important to have long lasting protection, a high percent of the longer, less volatile molecule is used.

As stated above, the shorter chains preferably have between about 6 and about 8 carbon atoms per molecule and the longer chains preferably have between about 8 and about 12 carbon atoms per molecule.

For example, the shorter chain component can vary between 1% and 99% of the active ingredients. More preferably it varies between about 10% and about 90% of the active ingredients. Alternatively, it varies between about 40% and about 60% of the active ingredients. The longer chain component can also vary between 1% and 99% of the active ingredients. More preferably it varies between about 10% and about 90% of the active ingredients. Alternatively, it varies between about 40% and about 60% of the active ingredients.

For many application it is most desirable to have three or more volatility ranges present in the active ingredients. One example would be a mixture in which relatively short, intermediate, and long chains would be present. The percentages with which these components are mixed for a given application will quickly become apparent to one of ordinary skill in the art. When mixing more than two unbranched chain sizes in the repellent, the shorter chain component preferably has between about 6 and about 8 carbon atoms per molecule, the intermediate chain component has between about 8 and about 9 carbons per molecule, and the relatively longer chain component has between about 9 and about 12 carbons per molecule.

The high volatility component can vary between 1% and 99% of the active ingredients. More preferably it varies between about 10% and about 70% of the active ingredients. Alternatively, it varies between about 20% and about 50% of the active ingredients. The intermediate volatility component can vary between 1% and 99% of the active ingredients. More preferably it varies between about 10% and about 70% of the active ingredients. Alternatively, it varies between about 20% and about 50% of the active ingredients. The lowest volatility component can vary between 1% and 99% of the active ingredients. More preferably it varies between about 10% and about 70% of the active ingredients. Alternatively, it varies between about 20% and about 50% of the active ingredients.

Among molecules having unbranched carbon chains, those molecules having shorter chains have higher volatility than longer chains. Additional modifications in volatility of the component compounds are made by modifying the branching of the chains. Generally branching on a chain increases volatility.

The inventive repellent comprises a novel combination of organic molecules, having different evaporation rates, where vapor pressure is related to the evaporation rate. Thus, one formulation of the inventive repellent comprises a mixture of three straight chain molecules, such as octanoic acid, nonanoic acid, and decanoic acid. An alternate formulation comprises a mixture of, for example, straight chain C-10 (decanoic acid) combined with branched ten-carbon molecules such as 4-methyl nonanoic acid. Any combination organic molecules having the appropriate volatilities to balance immediate and long-term effectiveness may be used to formulate the inventive repellent. Straight chain and branched chain organic molecules are combined to achieve this balance as well as combinations of straight-chain lengths or branched-chain molecules having the same or different numbers of carbons. The choice of which organic molecules to use in the inventive repellent is governed by factors such as commercial availability, cost, repellency, evaporation rate, odor, and stability.

Review of literature in the general field of the invention:

There is ample evidence that human skin emanates both attractant and repellent compounds for mosquitoes. No single compound is likely responsible for mosquito attraction; the same can be said for mosquito repulsion. The interaction of these compounds is probably of importance in the overall response of the mosquito. Brown (Brown A. W. A., H. P. Roessler, E. Y. Lipsitz and A. G. Carmichael. Factors in the attractiveness of bodies for mosquitoes. The Canadian Entomologist 96:102–103, 1964.) lists a number of factors involved in the attraction of mosquito to man (in order of importance): moisture, convective heat, carbon dioxide, movement, contour or increase in black-white interfaces, and reflectivity. The influence of carbon dioxide as a mosquito "activator" has long been recognized (Rudolphs, W. Chemotropism of mosquitoes. New Jersey Agricultural Experiment Station Bulletin No. 367, 1922). However, Acree and coworkers (Acree, F, R. B. Turner, H. K. Gouck, M. Beroza and N. Smith. L-Lactic Acid: A mosquito attractant isolated from humans. Science, 161:3846-7, 1968) have shown that carbon dioxide does not attract mosquitoes in purified air alone. Thiel and Laarman found that air swept over the arm was attractive even though carbon dioxide and moisture had been removed; they concluded the presence of other attractants or odors was responsible for the attraction (Van Thiel, P. H. and J. J. Laarman. What are the reactions by which the female Anopheles find its blood supplies? Acta Leidensia 24:180–187, 1954). Snow (Snow, W. F. The effect of a reduction in expired carbon dioxide on the attractiveness of human subjects to mosquitoes, Bull. Ent. Res. 69:43–48, 1970) studied mosquito attraction to normal subjects and to subjects wearing a breathing apparatus to remove most of the exhaled carbon dioxide. Fewer mosquitoes were attracted to the subjects with reduced carbon dioxide output. However, when the mosquitoes were in close range of the host, the experimental treatment had no effect on the proportion of mosquitoes attempting to feed. Snow concludes from this study that carbon dioxide, originating from the lung, may be more important as a long range attractant. Reports by Rahm (Rahm, U. Zum problem der attraktion von stechmucken durch den menschen, Acta Trop., 13:319–344, 1956) and Brouwer (Brouwer, R. The attraction of carbon dioxide excreted by the skin of the arm of malaria mosquitoes, Trop Geogr. Med. 12:62–66, 1960) showed that carbon dioxide output from the skin was insignificant in stimulating mosquitoes. In contrast to these findings, Khan et al. (Khan, A. A., H. I. Maibach, W. G. Strauss, and W. R. Fenley. Quantitation of effect of several stimuli on the approach of *Aedes aegypti*, J. Econ. Entomology 59:690–694, 1966) concluded that heat and carbon dioxide are important for the approach of mosquitoes to the host at close proximity, and that odor was more important at greater distance. Carlson et al. (Carlson, D. A., C. E. Schreck, and R. J. Brenner, Carbon dioxide released from human skin: effect of temperature and insect repellents; Journal of Medical Entomology 29:165–170, 1992) measured the amount of carbon dioxide given off by the hand at 1.0–1.8 ml/h under laboratory conditions. The authors concluded that this amount of carbon dioxide is negligible compared to ambient levels and was unlikely to be attractive to mosquitoes by itself.

In 1958, Brouwer (Brouwer, R., Acad. Proefschr. Leiden, 110p, 1958) reported consistent differences in attraction of *Anopheles stephensi* to humans that were independent of moisture, warmth and carbon dioxide. He concluded that the differences were due to sweat or body odor. Schreck (Schreck, C. E. and J. James, Broth culture of bacteria that attract female mosquitoes, Mosquito News 28:33–38, 1968) reported that a polyethylene glove, worn for 1 hour, remained attractant to mosquitoes over a 3 hour period after removal from the hand. Thompson and Brown demonstrated the attractiveness of sweat was decreased by the release of volatile acids (Thompson, R. P. and A. W. A. Brown; The attractiveness of human sweat to mosquitoes and the role of carbon dioxide; Mosquito News 15:80–84, 1955).

Gilbert et al. studied 50 men and 50 women to determine their attractiveness to Aedes aegypti mosquitoes (Gilbert, I. H. G. K. Gouck and N. Smith; Attractiveness of men and women to Aedes aegypti and relative protection time obtained with DEET; The Florida Entomologist 49:53–66, 1966). The 50 women subjects were, on average, less attractive than the 50 men. However, there was considerable overlap in the ranges of attraction, and many of the women were more attractive than some of the men. However, only two of the most attractive 10 subjects were women, and all of the least attractive 10 were women. A possible relationship between attraction and differences in skin lipid composition was not investigated. Roessler hypothesized that changes in the attractiveness of females with the menstrual cycle were caused by changes in estrogen evaporation from the skin (Roessler, P.; The attractiveness of steroids and amino acids to female Aedes aegypti; Proceedings of the Fiftieth Annual Meeting, New Jersey Mosquito Extermination Association and Nineteenth Annual Meeting, American Mosquito Control Association, Atlantic City, March 1963, pp. 250–255).

In a 1968 report, Acree et al. found a correlation between the attractiveness of individuals to mosquitoes and the quantity of lactic acid present in acetone washings of hands. Attractive material was first obtained by condensation of a nitrogen stream above the skin. However, the amount of material obtained was too small for analytical methods available at that time. These workers noted that the attractancy of lactic acid was not evident without the presence of carbon dioxide.

Price et al studied the attraction of mosquitoes to human emanations in a dual port olfactometer (Price, G. D., N. Smith and D. A. Carlson; The attraction of female mosquitoes (*Anopheles quadrimaculatus* SAY) to stored human emanation in conjunction with adjusted levels of relative humidity, temperature, and carbon dioxide; J. Chemical Ecology 5:383–395, 1979). Mosquitoes (female *Anopheles quadrimaculatus* SAY) were preferentially attracted to the "emanation" air, even though excess carbon dioxide or water had been added to control air without emanations.

In 1961, Brown and Carmichael reported that lysine free base was a mosquito attractant (Brown, A. W. A. and A. G. Carmichael; Lysine as a mosquito attractant; Nature 169:508–509, 1961). Lysine was known to be present in human sweat (Hier, S. W. T. Cornbleet and 0. Bergeim; J. Biol. Chem. 166:327, 1946). Although other amino acids had mosquito attractant properties, they were considerably less attractant than lysine. The attractiveness of lysine was later found to be proportional to the presence of carbon dioxide (Lipsitz, E. Y. and A. W. A. Brown; Studies on the responses of the female Aedes mosquito: IX The mode of attractiveness of lysine and other amino acids; Bull. Entomo. Res. 54 675–687, 1964).

Strauss et al., surveyed hospitalized patients with various diseases and taking various medications for their attractiveness to mosquitoes by a mosquito probing technique. No drug, vitamin, or disease was associated with unattractiveness, with the possible exception of untreated myxedema (Strauss, W. G. H. I. Maibach and A. A. Kahn; Drugs and disease as mosquito repellents in man; Am. J. Trop Med. Hyg. 17:461–464, 1968).

In addition to the compounds mentioned above, USDA investigators have studied 1-octen-3-ol as a mosquito attractant (Kline, D. L. D. A. Dame and M. V. Meisch; Evaluation of 1-octen-3-ol and carbon dioxide as attractants for mosquitoes associated with irrigated rice fields in Arkansas; J. Am. Mosq. Control Assoc. 7:165-9, 1991). Israeli investigators found that although sheep were attractive to *Culex pipiens* L. and *Aedes caspius* (Pallas), few *Culex pipiens* and no *Aedes caspius* engorged. The investigators suggested that sheep may possess, in addition to the mechanical protection afforded by wool, a close-acting repellent that deters the mosquitoes from biting. The repellent was not identified.

Maibach and coworkers report the observation that the attractancy of human sweat increased significantly when lipids were removed (Maibach, H. I. A. A. Khan, W. G. Strauss and W. A. Skinner; Human skin in relationship to mosquito attraction and repulsion; Connecticut Medicine, 33:23–28, 1969). Schreck and coworkers isolated a material from glass beads previously handled by humans (Schreck, C. E., N. Smith, D. A. Carlson, G. D. Price, D. Haile and D. R. Godwin; A material isolated from human hands that attracts female mosquitoes; Journal of Chemical Ecology, 8:429–438, 1981). This residue was found to be attractant to female *Aedes aegypti* and *Anopheles quadrimaculatus* Say mosquitoes. This residue was characterized as volatile, and stable on refrigerated storage for up to 60 days. The residue was not purified or chemically analyzed. Skinner et al. obtained human skin-surface lipids from ether washings of elbows from a number of volunteers (Skinner, W. A. H. C. Tong, H. I. Maibach and D. Skidmore; Human skin-surface lipid fatty acids—mosquito repellents; Experientia 26:728–730, 1970). This mixture was found to be repellent to Aedes aegypti mosquitoes. Vacuum distillation, gas chromatography and thin layer chromatography were used to isolate components from the mixture. The organic fraction of the lipids contained only weakly repellent unsaturated hydrocarbons, with the major repellent activity present in the more polar fractions. Straight chain carboxylic acids from C-5 to C-13 were found to have repellent activity in olfactometer tests; higher homologs from C-14 to C-18 had little repellent activity. Straight chain unsaturated carboxylic acids from C-9 to C-24 were also found to have repellent activity. Skinner concluded that unsaturated fatty acids accounted for the repellency of the free fatty acid fraction of skin surface lipids, based on two findings: 1) no saturated fatty acids below $C_{13}$ were detected and higher homologs had little repellent activity in olfactometer tests, 2) unsaturated fatty acids starting with $C_{14}$ were detected and these had repellent activity in olfactometer tests. Skinner then suggested that mosquito attraction to animals could be reduced by increasing the amount of unsaturated fatty acids present on the skin surface. To this end, 2-decenoic acid was tested for mosquito repellent activity in volunteers at Letterman Army Institute of Research in 1970 (Kurtz, A. P.; More Effective Topical Repellents Against Malaria-Bearing Mosquitoes: Review of Volunteer Tests of Mosquito repellent Formulations October 1969–September 1971, Report No. 13 (Interim Report), Letterman Army Institute of Research, Presidio of San Francisco, Calif. 94129, May 1, 1973). The compound was applied to the forearm at a dose of 0.5 $mg/cm^2$ and compared to DEET at the same dose. Application sites were challenged with Aedes aegypti mosquitoes. Although 2-decenoic acid showed repellent activity, its average duration of protection was shorter than that of DEET and its range of protection time was larger than that of DEET (Table 2). Skinner also reported the evaluation of a number of unsaturated fatty acids on the skin of man (Table 3). However, none provided longer protection time than DEET. It should be noted that this line of investigation was based on fatty acids recovered from skin surface wipes and not on the skin's chemical vapor, which is responsible for host seeking behavior. The significance of the volatile compounds was therefore underestimated.

TABLE 2

Test of Decenoic acid for repellency against Aedes aegypti on the skin of man (reference Kurtz, LAIR Report No. 13, 1973)[a]

| Compound | Protection Time (hours) | Protection Time Range (N) |
| --- | --- | --- |
| Decenoic acid 0.5 $mg/cm^2$ | 6 ± 4 | 0.5–12.5 (14) |
| DEET, 0.5 $mg/cm^2$ | 8 ± 2 | 3.5–12.0 (10) |

[a]A protection time of 0.5 h, observed for two subjects, indicated repellent failure at the first test period.

TABLE 3

Protection time of unsaturated carboxylic acids (0.31 $mg/cm^2$, reference Skinner, W.A., Attractiveness and Repellency of Man to Mosquito Bites, DTIC Report No. AD693891, October, 1969)

| Compound | Protection time against Aedes aegypti mosquitoes |
| --- | --- |
| 2-Nonenoic Acid (unsat C-9) | 2 h |
| 2-Decenoic Acid (unsat C-10) | <15 min. |
| Undecylenic Acid (unsat C-11) | 3.5 h |
| 2-Dodecenoic Acid (unsat C-12) | 2 h |
| Oleic Acid (unsat C-18) | <15 min. |
| Linoleic Acid (unsat C-18) | <15 min. |
| Linolenic Acid (unsat C-18) | <15 min. |
| Arachidonic Acid (unsat C-20) | <15 min. |
| DEET (reference) | 5.5 h |

A number of a straight chain carboxylic acids were reported in 1954 to have repellent activity (King, W. V., Chemicals evaluated as insecticides and repellents at Orlando, Fla. Agriculture Handbook No. 69; Entomology Research Branch, Agricultural Research Service, U.S. Department of Agriculture, Washington, D.C., 1954. p. 185). None, however, provided protection time equal to that of DEET (Table 4). Quintana and coworkers realized the short-comings of these compounds and attempted to improve their protection time by the preparation of carboxylic acid esters designed to adhere to the stratum corneum and slowly release the active component (free acid) on hydrolysis of the ester (Quintana, R. P., Lasslo, A., Garson, L. R., Chemical Studies in Connection with Potential Systemic Insect-Repellents and Prophylactic Agents Deposited in the Skin; Report No. 4, Research Contract No. DA-49–193-MD-2636, U.S. Army Medical Research and Development Command, Office of the Surgeon General, Washington, D.C. 20315). However, these compounds did not result in a repellent with improved duration of protection over DEET.

TABLE 4

Protection time of saturated carboxylic acids applied to human skin at a dose of approximately 2 mg/cm$^2$.[a]

| Compound | Protection time against yellow fever mosquitoes | Protection time against malaria mosquitoes |
| --- | --- | --- |
| Caproic Acid (C-6) | — | — |
| Ethanthic (C-7) | 121–180 min | 90+ min. |
| Caprilic Acid (C-8) | — | — |
| Pelargonic Acid (C-9) | 180+ min. | 31–60 min. |
| Capric Acid (C-10) | 300+ min. | 61–90 min. |
| Hendecanoic Acid (C-11) | 300+ min. | 90+ min. |
| Lauric Acid (C-12) | — | — |
| DEET (reference) | 363 min[b] | — |

[a]Except where noted, data taken from King, 1954, Chemicals evaluated as insecticides and repellents at Orlando, FLA., U.S. Department of Agriculture, Agricultural Research Service, Agriculture Handbook No. 69). Following negative skin-irritation tests on rabbits at the FDA, compounds were evaluated on the skin of 2 to 4 male human subjects. One ml of the compound was rubbed over one forearm (approximately 500 cm2). A glove was worn to protect the untreated hand while the treated forearm was exposed in a cage containing a high number (2,000–4,000) of unfed mosquitoes for 3 minutes at intervals of approximately 30 minutes until two bites were received (two bites in one test period or one bite in each of two consecutive test periods). The time interval between application and when two bites were received was defined as the "protection time". Against the yellow fever mosquito (Aedes aegypti (L.)), ethanthic acid (C-7) was rated 3 (121–180 min) pelargonic acid (C-9) was rated 4 (180+ min), capric acid (C-10) was rated 4A (300+ min.) and hendecanoic acid (C-11) was rated 4A (300+ min.). Against the malaria mosquito (*Anopheles quadrimaculatus* Say), ethanthic acid was rated 4 (90+ min.), pelargonic acid was rated 2 (31–60 min), capric acid was rated 3 (61–90 min.) and hendecanoic acid was rated 4 (90+ min.).
[b]Data from Gilbert, I.H., Gouck, H.K. and C.N. Smith. 1957, New insect repellent, Soap and Chemical Specialties, 33: 115–133.

In a later report, Skinner et al. analyzed acetone extracted lipids from skin using gas chromatography-mass spectroscopy (Skinner, W. A., H. C. Tong, H. Johnson, R. M. Parkhurst, D. Thomas, T. Spencer, W. Akers, D. Skidmore and H. Maibach; Influence of human skin surface lipids on protection time of topical mosquito repellent; J. Pharm. Sci., 66:1764–1766, 1977). Multiple regression analysis was used to relate attractancy and repellent protection time to the amounts of saturated and unsaturated fatty acids. Dry protection time or duration of protection of the insect repellent N,N-diethyl-3-benzamide (DEET) correlated positively with saturated fatty acids C-11, C-13, C-15 and C-18 and unsaturated fatty acids C-14, C-15, C-16 and C-17; dry protection time correlated negatively with saturated C-7, C-12 and C-16 fatty acids. The fatty acids may affect the protection time of DEET by a physical mechanism; that is, they may alter the evaporation and penetration of DEET through their film forming activity. Indeed, repellent protection time of DEET correlated positively with the total weight of lipid found on the skin. Attractancy, as measured by the average number of Aedes aegypti mosquitoes probing the test site of the volunteer in one minute, was found to correlate positively with C-15 unsaturated fatty acid and C-14 saturated fatty acid; attractancy was found to correlate negatively with the more volatile C-11 saturated fatty acid. The authors indicated that the precise identification of fatty acid components affecting attractiveness would require further study.

There is ample evidence that human skin emanates both attractant and repellent compounds for mosquitoes. However, skin emanations have been poorly characterized, and important volatile components were lost in the analysis procedures (Bowen, M. F., The sensory physiology of host-seeking behavior in mosquitoes. Annu. Rev. Entomol., 36:139–158, 1991). No single compound is likely responsible for mosquito attraction; the same can be said for mosquito repulsion. Although certain fatty acids were found to repel mosquitoes, a practical insect repellent has never been developed from these compounds because it was not appreciated that optimal evaporation rates from the skin were not achieved. We have developed a long lasting repellent based on a combination of fatty acids, each with the appropriate volatility.

EXAMPLES OF THE INVENTIVE INSECT AND ARTHROPOD REPELLENT

EXAMPLE 1: Identification of natural insect repellent compounds on human skin

Olfactometer: A Fiensod and Spielman olfactometer, as modified by Bowen and Davis, measured the host-oriented flight response of female mosquitoes to volatile host emanations (Feinsod, F. M., and A. Spielman; An olfactometer for measuring host-seeking behavior of female Aedes aegypti (Diptera:Culicidae); J. Med. Entomol., 15:282–285, 1979). The olfactometer (approximately 38 cm high) consisted of an upper and lower screened chamber with a closure between the chambers (FIG. 8). A fan placed above the upper chamber drew air through the apparatus at approximately 0.2 m/s. A temperature and humidity controlled chamber (5' wide by 6' long by 8'- high) was constructed to house the test subject and the olfactometer.

Rearing of Mosquitoes: A second environmental chamber, maintained at 27° C. and 80% humidity, was dedicated to the rearing of Aedes aegypti mosquitoes. Routine shipments of eggs (American Biological Supply, Gainesville, Fla.) were used to maintain a continuous supply of adult 5–10 day old mosquitoes.

Assays for Attraction of Mosquitoes to Human Subjects: A group of 30 volunteers, consisting of 14 females and 16 males and ranging in age from 24 to 68 years, was selected from the surrounding civilian population. Individuals were tested for their ability to attract Aedes aegypti mosquitoes contained in the olfactometer. Tests were conducted at a temperature of 27° C. and 50% relative humidity. For each trial 15 avid adult female *Aedes aegypti* mosquitoes (5–10 days post-emergence) were placed in the upper chamber. A small fan was placed on top of the upper chamber to cause an air flow from the lower chamber to the upper chamber. A trial began when the closure between the upper and lower chamber was opened in the absence of a human host. The number of mosquitoes entering the lower chamber within a 3 minute period was recorded. The volunteer then placed his or her arm beneath the lower chamber and the number of mosquitoes flying from the upper chamber to the lower chamber was recorded for the time intervals 0–1, 1–3, 3–5 and 5–7 minutes. This trial was repeated twice during a test session to obtain three replicates. Two additional test sessions, at time intervals of at least 1 week, were conducted to obtain at least 8–9 replicates for each of 24 subjects. Of the remaining 6 subjects, 3 were tested on two separate occasions for a total of 6 replicates per subject; 3 were tested on one occasion for a total of 3 replicates per subject. A total of 254 tests were conducted.

Olfactometer scores were calculated for each trial by dividing the number of mosquitoes entering the lower chamber of the olfactometer during the 0–1, 1–3, 3–5 and 5–7 minute intervals by the number of mosquitoes remaining in the upper chamber of the olfactometer at the end of the 3 minute control period. The fractions so obtained was plotted versus time. An equation was fitted to the data and the area under the curve (olfactometer score) was calculated. An area of 0 (0 mosquitoes entering the lower chamber ×7 minutes) would indicate the subject was completely unattractive to mosquitoes. A area of 7 would indicate maximum attraction.

Human subjects were identified from a group of 30 males and females whose forearms were consistently least attractive to Aedes aegypti mosquitoes contained in an olfactometer (Table 5). Subjects were also identified who were consistently most attractive to mosquitoes (Table 5). All of the 4 least attractive subjects were female and 10 of the 12 least attractive subjects were female. All of the 5 most attractive subjects were male and 10 of the 12 most attractive subjects were male. Females in general were significantly less attractive to the mosquitoes than the males (ANOVA, F=49.33, P=0.0000). The histograms of olfactometer response for all trials with female subjects is given in FIG. 9. The corresponding data for male is given in FIG. 10. Olfactometer response did not significantly correlate (P>0.05) with age of male or female subjects (FIGS. 11 and 12).

TABLE 5

Olfactometer response of 30 human subjects to mosquitoes.

| Subject No. | Olfactometer Response[a] | No. of Replicates |
|---|---|---|
| 30 (Female)[b] | 1.73 ± 0.67 | 3[c] |
| 24 (Female)[b] | 2.13 ± 1.13 | 9 |
| 15 (Female)[b] | 2.65 ± 0.53 | 8 |
| 29 (Female)[b] | 2.79 ± 1.44 | 9 |
| 18 (Female) | 3.01 ± 1.19 | 9 |
| 26 (Male) | 3.06 ± 0.97 | 9 |
| 16 (Female) | 3.26 ± 1.10 | 9 |
| 1 (Female) | 3.34 ± 1.35 | 18 |
| 3 (Male) | 3.47 ± 1.52 | 10 |
| 27 (Female) | 3.56 ± 1.39 | 9 |
| 11 (Female) | 3.60 ± 1.19 | 9 |
| 28 (Female) | 3.65 ± 0.53 | 6 |
| 25 (Male) | 3.67 ± 1.49 | 6 |
| 23 (Male) | 3.82 ± 1.05 | 9 |
| 12 (Female) | 4.08 ± 1.18 | 9 |
| 10 (Female) | 4.22 ± 1.63 | 3 |
| 22 (Male) | 4.25 ± 0.92 | 9 |
| 17 (Male) | 4.33 ± 0.94 | 9 |
| 6 (Female) | 4.39 ± 1.51 | 9 |
| 13 (Male) | 4.44 ± 1.36 | 9 |
| 5 (Male) | 4.45 ± 0.62 | 9 |
| 20 (Male) | 4.74 ± 0.68 | 9 |
| 4 (Female) | 4.92 ± 0.88 | 9 |
| 19 (Male) | 4.93 ± 0.99 | 3 |
| 21 (Male) | 5.03 ± 0.84 | 6 |
| 14 (Male)[b] | 5.06 ± 1.11 | 9 |
| 7 (Male)[b] | 5.20 ± 1.11 | 9 |
| 9 (Male)[b] | 5.21 ± 0.85 | 9 |
| 2 (Male)[b] | 5.31 ± 0.73 | 11 |
| 8 (Male)[b] | 5.32 ± 0.76 | 9 |

[a]Olfactometer response (mean ± S.D.) was calculated as the area under the curve of fractional mosquito response versus time profile. A hypothetical test subject completely unattractive to mosquitoes would have a score of zero. A maximally attractive subject would have a score of almost seven.
[b]Olfactometer response scores were analyzed by ANOVA and the Student-Newman-Keuls Multiple Range Test, which identified subjects Nos. 15, 24, 29, and 30 as least attractive to mosquitoes and subjects Nos. 2, 7, 8, 9, and 14 as most attractive to mosquitoes. Each of the four least attractive female subjects were significantly different from all of the five most attractive male subjects (Tukey's test, P < 0.05).
[c]Subject 30 was retested on a separate occasion with even lower olfactometer scores; however, the mosquitoes were exposed to low temperatures from an equipment malfunction and the results are not included.

EXAMPLE 2: Assay of Compounds for Mosquito Repellency on Gauze or Polyester Film Test compounds were dissolved in acetone or ethanol at a concentration of 150 mg/5 cc. Ethanol solutions of carboxylic acids were prepared just prior to use. Five hundred microliters of these solutions were applied to a 50 $cm^2$ circular area of a single layer of cotton gauze (Curity Curad gauze, Futuro Inc., Milford, Ohio) or nonwoven polyester film (Reemay 2250, Reemay/Tycon, Inc.). The resultant dose was 0.3 mg/$cm^2$. Treated gauze or film was allowed to dry in a hood for 3 minutes prior to placement in a cylindrical stainless steel cup (9 cm in diameter and 3 cm in height), whose bottom consisted of stainless steel screen. The cup was attached to the bottom of the olfactometer (FIG. 8) so that air flowed through the stainless steel screen of the cup, through the treated gauze or film, and through the olfactometer. A volunteer's forearm was placed under the cup, so that air drawn into the cup and olfactometer was laden with human skin emanations. Tests were conducted as described in the preceding paragraph, "Assays for attraction of mosquitoes to human subjects". Percent repellency was determined from the fraction of mosquitoes entering the lower chamber over a seven minute period.

This assay is an approximate measure of the intrinsic repellency of a compound. Good repellency in this test is a necessary, but not sufficient, condition for good repellency on skin. Mosquito repellents must produce a vapor over the skin surface to confuse the host seeking behavior of the insect. However, volatilization must not be so great that the repellent action rapidly dissipates. Since volatilization from the skin will be different from an inanimate surface, skin tests are necessary to confirm that a compound will be a practical repellent.

Percent repellency results for various compounds are contained in Table 6. Three of the compounds tested (3M2OCTEN, 3M2PENTEN, and valerolactam) were found only on the skin of females (Zeng, X. Leyden, J. J. Spielman, A. I. and Preti, G., 1996, Analysis of characteristic human female axillary odors: qualitative comparison to males; J. Chem. Ecol. 22:237–257). 3M2OCTEN exhibited the greatest repellency (95%), 3M2PENTEN repellency (65%) was similar to that of DEET (74%), and valerolactam had essentially no repellent activity (20%).

TABLE 6

Percent repellency for various compounds (applied to cotton gauze or polyester film at a dose of 0.3 mg/$cm^2$) against Aedes aegypti mosquitoes[a].

| Test Compound | Carbon Atoms | Percent Repellency | N |
|---|---|---|---|
| Ethanol | 2 | 7 ± 9 | 5 |
| Acetone | 3 | 12 ± 10 | 12 |
| Pentanoic acid[b] (C-5) (valeric acid) | 5 | not tested | — |
| 2-Pentenoic Acid (2PENTEN) | 5 | 100 ± 0 | 2 |
| Valerolactam | 5 | 20 ± 22 | 3 |
| 3-Methylpentanoic Acid (3MPENTAN) | 6 | 43 ± 14 | 2 |
| 3-Methyl-2-pentenoic Acid (3M2PENTEN) | 6 | 65 ± 16 | 3 |
| Octanoic Acid (C-8) | 8 | 87 ± 1 | 2 |
| 2-Octenoic Acid (2-OCTEN) | 8 | 97 ± 5 | 2 |
| 4-Methyloctanoic acid (4MOCTAN) | 9 | 88 ± 18 | 2 |
| 3-Methyl-2-octenoic acid (3M2OCTEN) | 9 | 95 ± 6 | 6 |
| Nonanoic acid (C-9) | 9 | 97 ± 5 | 2 |
| Decanoic acid (C-10) | 10 | 100 ± 0 | 2 |
| Undecanoic acid (C-11) | 11 | 93 ± 0 | 2 |

TABLE 6-continued

Percent repellency for various compounds (applied to cotton gauze or polyester film at a dose of 0.3 mg/cm$^2$) against Aedes aegypti mosquitoes[a].

| Test Compound | Carbon Atoms | Percent Repellency | N |
|---|---|---|---|
| Lauric acid (C-12) | 12 | 69 ± 23 | 3 |
| N,N-Diethyl-m-toluamide (DEET) | 12 | 74 ± 12 | 3 |

[a]Tests were conducted 3 minutes after application of test compounds.
[b]Pentanoic acid was not tested because of its highly offensive odor.

All of the octanoic acid derivatives had good repellent activity, in the range of 87–97% repellency. The pentanoic acid derivatives were generally less repellent (43–65%); however, 2-pentenoic acid had 100% repellency. Nonanoic acid (C$_9$ straight chain), decanoic acid (C$_{10}$ straight chain), and undecanoic acid (C$_{11}$ straight chain) had good repellency (93–100%). Lauric acid (C$_{12}$ straight chain) had lower repellency (69%), similar to DEET. Mosquito repellent activity has not been previously reported for the octanoic acid derivatives 3M2OCTEN, 2OCTEN, 4MOCTAN, and the pentanoic acid derivatives 3M2PENTEN, 2PENTEN, and 3MPENTAN. Repellent activity has been reported for the straight chain saturated carboxylic acids and certain unsaturated carboxylic acids (See Tables 2, 3 and 4). Some of the saturated carboxylic acids have also been investigated as mosquito attractants (Knols, B. G. J., 1996, Odour-mediated host-seeking behavior of the afro-tropical malaria vector Anopheles Gambiae Giles; Thesis. ISBN: 90-5485-487-1; Wageningen Agricultural University; The Netherlands; pp. 213). The results, however, were inconclusive.

In addition to carboxylic acids, alkanes, alkenes, alcohols, aldehydes, ketones, acids and lactones are known to exist on the skin surface (Zeng, X., Leyden, J. J., Lawley, H. J., Kiyohito, S., Isao, N., and Preti, G. 1991, Analysis of characteristic odors from human male axillae, Journal of Chemical Ecology, 17:1469–1492) or to volatilize from the skin surface (Goetz, N., Kaba, G. Good, D. Hussler, G. and Bore, P., 1988, Detection and identification of volatile compounds evolved from human hair and scalp using headspace gas chromatography, Journal of the Society of Cosmetic Chemists, 39:1–13). Repellent activity is known to exists in alcohols, aldehydes, ketones, acids (King, W. V., Chemicals evaluated as insecticides and repellents at Orlando, Fla., U.S. Department of Agriculture, Agricultural Research Service, Agriculture Handbook No. 69) and lactones (Weeks, M. H. and DeSena, B. J. Topical Hazard Evaluation Program of Candidate Insect Repellent AI3-36030 delta-Dodecalactone, U.S. Army Environmental Hygiene Agency, Aberdeen Proving Ground, Md., Defense Technical Information Report No. ADA 040974, March 1976-April 1977).

EXAMPLE 3: Assay of Compounds for Mosquito Repellency on Skin

Test compounds were dissolved in acetone or ethanol at a concentration of 300 mg/5 cc. Ethanol solutions of carboxylic acids were prepared just prior to use. Three hundred and fifty microliters of these solutions were applied to a 70 cm$^2$ rectangular area of the forearm. The resultant dose was 0.3 mg/cm$^2$. The repellent treated area was allowed to dry for 5 minutes prior to test. The treated skin area was placed under the olfactometer and tests were conducted as described in the preceding paragraph, "Assays for attraction of mosquitoes to human subjects". Percent repellency was determined from the fraction of mosquitoes entering the lower chamber over a seven minute period.

A number of compounds were preliminarily investigated for their ability to act as mosquito repellents after topical application (Table 7). Some of the more volatile acids (octanoic acid and 4MOCTAN) had mean repellency (87–93%) that was competitive with that of DEET (95%) shortly after application (0 hr). At 2 hours after application, DEET repellency remained high (89%), while the highest repellency for carboxylic acids (66–73% mean repellency) was found in three of the acids containing 9 carbons (3M2OCTEN, 4MOCTAN, and nonanoic acid). The pentanoic acid derivatives were not tested because two of the derivatives had low repellency on the gauze/polyester film tests (Table 6) and because these derivatives are considerably more volatile that DEET (Table 7). The compound 2-ethyl-1,3-hexanediol, once a commercial insect repellent, is twice as volatile as DEET and protects against mosquitoes for 3–4 hours as compared to 5–6 hours for DEET (Hill, J. A., Robinson, P. B., McVey, D. L., Akers, W. A., and Reifenrath, W. G. 1979; Evaluation of mosquito repellents on the hairless dog; Mosquito News (Journal of the American Mosquito Control Association), 39:307–310). Therefore, the pentanoic acid derivatives, having volatilities 17–30 times that of DEET, were not expected to provide long lasting repellency; these compounds are too volatile and serve as an upper bound of vapor pressure for a practical repellent for carboxylic acids. Decanoic, undecanoic, and dodecanoic acids were less volatile than DEET and had lower 0-h repellency than DEET (Table 7). Dodecanoic acid demonstrated no repellent effect on skin (Table 7), despite having 93% repellency after application to gauze/polyester film (Table 6). This compound was probably not sufficiently volatile from skin and provided a lower bound of vapor pressure for a practical repellent for carboxylic acids.

TABLE 7

Percent repellency for various compounds at various times after application against Aedes aegypti mosquitoes[a]

| Compound | Carbon Atoms | Vol.[b] | Percent Repellency (N) | | | |
|---|---|---|---|---|---|---|
| | | | 0 h | 2 h | 4 h | 8 h |
| No Treatment | 0 | — | 9 ± 7 (4) | 13 ± 12 (3) | 4± 6 (2) | 17 (1) |
| 2-Pentenoic acid (2PENTEN) | 5 | 92 (est) | — | — | — | — |
| 3-Methyl-2- | 6 | 49.5 | — | — | — | — |

TABLE 7-continued

Percent repellency for various compounds at various times after application against Aedes aegypti mosquitoes[a]

| Compound | Carbon Atoms | Vol.[b] | Percent Repellency (N) | | | |
|---|---|---|---|---|---|---|
| | | | 0 h | 2 h | 4 h | 8 h |
| pentenoic acid (3M2PENTEN) | | (est) | | | | |
| 3-Methypentanoic acid (3MPENTAN) | 6 | 49.5 (est) | — | — | — | — |
| Hexanoic acid | 6 | 39.6 | — | — | — | — |
| Octanoic acid (C-8) | 8 | 10.8 | 93 (1) | 36 (1) | — | — |
| 2-Octenoic acid (2-OCTEN) | 8 | 10.8 (est) | 50 (1) | 29 (1) | 27 (1) | — |
| 2-Ethyl-1,3-hexanediol (6-12) | 8 | 6 | — | — | — | — |
| 3-Methyl-2-octerioic acid, 0.3 mg/cm$^2$ (3M2OCTEN) | 9 | 6 (est) | 70 ± 24 (2) | 40 ± 5 (3) | 47 ± 21 (3) | 60 (1) |
| 3-Methyl-2-octenoic acid, 0.6 mg/cm$^2$ (3M2OCTEN) | 9 | 6 (est) | 66% (1) | 73% (1) | 40 (1) | — |
| 4-Methyloctanoic acid (4MOCTAN), 0.3 mg/cm$^2$ | 9 | 6 (est) | 87 (1) | 66 (1) | — | — |
| 4-Methyloctanoic acid (4MOCTAN), 0.6 mg/cm$^2$ | 9 | 6 (est) | 93 ± 0 (2) | 79 ± 21 (2) | 67 ± 9 (2) | — |
| Nonanoic acid (C-9) | 9 | 4.8 | 76 ± 14 (2) | 66 (1) | 47 (1) | — |
| N,N-Diethyl-m-toluamide (DEET) | 12 | 3 | 95 ± 6 (3) | 89 ± 10 (3) | 83 ± 9 (3) | — |
| Decanoic acid (C-10) | 10 | 2.4 | 73 (1) | 53 (1) | 73 (1) | — |
| 2-Decenoic acid (2DECEN) | 10 | 2.4 (est) | — | — | — | — |
| Ondecanoic acid (C-11) | 11 | 1.5 (est) | 40 (1) | — | — | — |
| Dodecanoic acid (C-12) | 12 | 0.57 (est) | 0 (1) | — | — | — |

[a]Compounds applied at a dose of 0.3 mg/cm$^2$, unless otherwise indicated, to one subject.
[b]Vapor pressure in mm Hg at 125° C. Values were obtained from the literature (Handbook of Chemistry and Physics, 1996; D. R. Lide and H. P. R. Frederikse, eds., 76th ed., CRC, Boca Raton, pp. 6–77 to 6–108; and Blame, R. L. and Levy, P. F., 1974, The use of thermal evolution analysis (TEA) for the determination of vapor pressure of agricultural chemicals, Anal. Calorimetry 3: 185–198). Certain values designated "(est)" were estimated or extrapolated from literature values.

EXAMPLE 4: Design of Long Lasting Repellent Formulation

Octanoic acid, the eight carbon fatty acid, had the highest volatility of any of the carboxylic acids tested on skin (Table 7) and provided the best initial repellency (0-h). However, octanoic acid's repellency rapidly decayed to only 36% at 2-h and reflected the exponential or first order evaporative loss of the compound from the skin surface. The exponential change in the evaporation rate of DEET from the surface of excised pig skin is given in FIG. 13. The change in the evaporation rate of, for example, octanoic acid from the skin surface would be even greater because it is more volatile than DEET. A repellent is only effective while the evaporation rate is greater than its MEER (minimum effective evaporation rate). For DEET that is between about 10 and 15 $\mu$gm/cm$^{2-}$ hr, as shown by the straight line in FIG. 13. An impractically large increase in the initial dose, or application level, would be required to extend protection time of molecule with a high evaporation rate. FIG. 13 also shows the change in the evaporation rate of the novel inventive repellent, formulated with equal parts octanoic, nonanoic, and decanoic acids. In contrast to DEET, the inventive repellent's change in evaporation rate levels off above the MEER.

Decanoic acid, the ten carbon fatty acid, had the lowest volatility of any carboxylic acid which provided at least 50% protection at 0-h. In contrast to octanoic acid, its protection remained relatively constant (Table 7), and reflected its constant or zero order evaporative loss from the skin surface (FIG. 13). Because of the compound's low volatility, it is not possible to significantly increase its evaporation rate from the skin surface merely by increasing the dose. Such a compound may provide a long duration of protection if its evaporation rate is just above the MEER or may fail immediately if its evaporation rate is just below the MEER. Test results for decenoic acid, a compound of similar volatility, are illustrative (Table 2). On two of the test subjects, the repellent failed immediately, while giving up to 12 hours of protection for other subjects.

The results for the nine carbon nonanoic acid (Table 7) are intermediate between the extremes of octanoic acid and decanoic acid. It is less repellent than octanoic acid at 0-h, but its repellency does not decay as rapidly. Increasing the dose of related nine carbon acids (3MOCTEN and 4MOCTAN) did not result in a significant increase in repellency that was competitive with DEET's at 4 hours (Table 7).

It was known that a mixture of two repellents will decrease their initial rate of evaporation and provide a higher level of evaporation at longer time points (Reifenrath et al., 1989, Evaporation and skin penetration characteristics of mosquito repellent formulations, Journal of the American Mosquito Control Association, 5:45-51). Based on this premise, repellents were made having a mixture of the eight, nine and ten carbon acids would provide long lasting protection. Test results (Table 8) for this mixture gave protection at 8 hours equivalent to that of DEET at 4 hours.

TABLE 8

Comparison of repellency (% repellency against Aedes aegypti) of N,N-diethyl-m-toluamide (DEET, 0.3 mg/cm², N = 3) and a mixture of n-octanoic, n-nonanoic, and n-decanoic acids (C8C9C10, 0.2 mg/cm² each, N = 3) on skin.

| Test Substance | % Repellency (0 hr) | % Repellency (2 hr) | % Repellency (4 hr) | % Repellency (8 hr) |
|---|---|---|---|---|
| C8C9C10 | 93 ± 1 | 85 ± 4 | 70 ± 19 | 82 ± 26 |
| DEET[a] | 95 ± 6 | 89 ± 10 | 83 ± 9 | — |

[a]Data for DEET taken from Table 7.

EXAMPLE 5: Mildness Additive for Formulations

Application of octanoic acid full strength to intact or abraded rabbit skin for 24 hours under occlusion produced moderate to severe irritation; full strength nonanoic acid produced moderate irritation; full strength decanoic acid produced moderate to severe irritation (Moreno, O. M., Reports to Research Institute for Fragrance Materials, Aug. 2, 1976, Aug. 22, 1977). When tested at 1% in petrolatum on the skin of human subjects, octanoic and decanoic acids produced no irritation or sensitization reactions. When tested at 12% in petrolatum on the skin of human subjects, nonanoic acid produced no irritation or sensitization reactions. Erythema was observed on the skin of human males after repeated applications of 0.5 M solutions of octanoic, nonanoic and decanoic respectively) under occlusive conditions (Stillman, M. A., Maibach, H. I. and Shalta, A. R., Relative irritancy of free fatty acids of different chain length. Contact Dermatitis 1:65-69, 1975).

Solutions containing 5% octanoic acid, 5% nonanoic acid, and 5% decanoic acid (C8C9C10) in ethanol and volatile silicone fluid (Dow Corning 345 fluid, CTFA designated cyclomethicone) were prepared. An aqueous gel containing 5% of each acid was also prepared. Their skin irritancy was compared to that of a commercial insect repellent (cream formulation of 10% DEET, Skintastic, S. C. Johnson, Racine WHEREIN) on the forearms of a male subject. C8C9C10 in alcohol and silicone solutions were applied at a volume of 0.5 ml to gauze pads that were placed on separate 1 inch×1 inch areas of skin; the C8C9C10/gel and DEET/cream formulations were applied at a mass of 0.5 g to separate sites. All sites were covered with a semi-occlusive tape (Transpore, 3M, Minneapolis, Minn.). Four hours after applications, sites were uncovered and washed with water. No erythema was observed with the C8C9C10/silicone formulation and slight erythema was observed with the DEET cream formulation; no erythema was observed at later time points (24, 48, 72 hours after application) for these two formulations. In contrast, the C8C9C10/aqueous gel formulation caused a burning sensation after application and this formulation, along with the C8C9C10/alcohol formulation resulted in erythema, sometimes severe, at 4, 24, 48 and 72 hours.

A Primary Dermal Irritation study of C8C9C10/silicone formulation and the commercial DEET cream formulation was conducted on six rabbits according to EPA, FIFRA Subdivision F guidelines. The protocol was similar to that outlined for the human exposure, except that application sites were totally occluded with a rubber dam for 4 hours. Both formulations were rated as mildly irritating in this test.

Octanoic, nonanoic and decanoic acid clearly have the potential to cause skin irritation and the degree of skin irritation will be a function of the formulation. Alcohol and aqueous gel formulations containing 5% of each acid do not appear acceptable for use as an insect and arthropod repellent in humans; a the silicone formulation however was found to be acceptable.

In addition to having the effect of reducing skin irritation, water insoluble silicon containing additives are known to impart water repellency to a topical formulation (Dow Corning Literature Code 2223926, Dow Corning Corporation, Midland, Mich.).

Volatile silicon fluids are available commercially. For example, Dow Corning uses commercial designations of 244, 245, 246, 344 and 345, which are mixtures of polydimethylcyclosiloxanes (cyclomethicones) and are composed of tetramers (e.g. cyclotetrasiloxane, octamethylcyclotetrasiloxane), pentamers (e.g. cyclopentasiloxane, decamethylcyclopentasiloxane), and hexamers (e.g. cyclohexasiloxane, dodecamethylcyclohexasiloxane).

The volatility of the vehicle can be important as well as the volatility of the active ingredients. The cyclomethicones are more volatile than typical repellent molecules, and are slightly less volatile than water. The cyclomethicones have a long history of use in cosmetic preparations. As vehicles, they allow good spreading of actives on the skin and will eventually evaporate. They are insoluble in water, so that resistance to water wash-off of actives is imparted. The cyclomethicones can be turned into gels for ease of application to the skin. Gelling of a formulation of octanoic, nonanoic, and decanoic acids (5% each in 344 fluid) did not interfere with repellent activity against mosquitoes in tests conducted as described in Example 3.

Dimethicone (hexamethyldisiloxane) has similar physical properties to the cyclomethicones and is also extensively used in cosmetics. A variety of polydimethylsiloxanes, with higher molecular weight than the cyclomethicones or dimethicone, enjoy wide use in cosmetics; however, because of their higher molecular weight, they are less volatile. They do provide alternative carriers to the cyclomethicones, or mixtures of the two can be used.

A wide variety of derivatives of the above compounds are obtained by introduction of various functional groups, by copolymerization, or by crosslinking and many of those can be used to make useful formulations of the inventive insect and arthropod repellent.

Mixtures of the various silicone fluids, either with other silicone fluids or non-silicon containing substances, are used in a variety of cosmetic preparations to impart special properties, to include water repellency and skin protection.

To insure that the addition of silicone fluid to the actives did not interfere with mosquito repellency, a comparison of the C8C9C10/silicone formulation with a commercial insect repellent formulation was conducted. A commercial formulation of DEET (Skintastic, S. C. Johnson, Racine,) was applied to a 100 cm$^2$ area on the forearm of 1 volunteer (subject 02) to give a dose of 0.3 mg/cm$^2$ of DEET. A formulation of C8C9C10 (5% octanoic, 5% nonanoic, 5% decanoic in Dow Corning 345 volatile silicone fluid) was applied to a 100 cm$^2$ on the subject's other arm to give a dose of 0.3 mg/cm$^2$ total acids. Application sites were placed under the olfactometer at 1, 2 and 4 hours after treatment. Untreated areas on each arm were placed under the olfactometer at the completion of the treated area tests to check the avidity of the mosquitoes. Tests were done on four separate test days. The results are shown in FIG. 14. The inventive C8C9C10/silicone formulation had repellency equal to the commercial formulation at the 1, 2 and 4 hour points (ANOVA, Tukey Studentized Range Method, P=0.05). Interestingly, C8C9C10/silicon at 0.3 mg/cm$^2$ total actives produced repellency (90±13% at 1 h, 81±14% at 2 h, and 74±22% at 4 hours) equal to unformulated C8C9C10 applied at 0.6 mg/cm$^2$ total actives (Table 8).

Thus, the invention provides a new formulation for use on human skin to repel insects and arthropods. The formulation is based on chemicals normally found on the human skin and so has a natural feel. It combines carbon chains having insect repellent activity at different vapor pressures, to achieve persistence over time on the skin and volatility for effectiveness in the volume of air surrounding the skin.

EXAMPLE 6: Veterinary Uses

Animal productivity is known to be reduced as a result of biting insects and arthropods. For example, stable flies reduce milk production by 5 to 10%. While the use of pesticides can sometimes provide a short term solution to this problem, the long term economic consequences of damage to non-target species, environmental pollution, and contamination of the food chain can be severe. The C8C9C10/silicone formulation provides a non-lethal and non-toxic method to protect animals as well as humans from nuisance and disease-carrying insects. This formulation is suitable for use in standard hand-held sprayers and would imparts water repellency.

Specifically, formulation of C8C9C10 (5% octanoic, 5% nonanoic, 5% decanoic acids) in Dow Corning 345 fluid was applied to membranes exposed to approximately 50 wild *Stomoxys calcitrans* (biting stable fly) contained in plastic tubes 8.5 cm tall and 5 cm in diameter. The membranes were mounted over warm defibrinated sheep blood. Untreated membranes served as controls. Flies were observed for 15–20 minutes, anesthetized, placed on a chill table, and sorted according to whether they had engorged blood or not. No flies engorged blood when the freshly treated membrane was tested and most flies became incapacitated; approximately 90% of flies exposed to the control membrane engorged (Table 9). A membrane treated with the repellent formulation 3 hours prior to stable fly challenge also prevented all flies from engorging; approximately 50% of flies exposed to the control membrane engorged (Table 9).

TABLE 9

Efficacy of formulation C8C9C10/DC345 (5% octanoic, 5% nonanoic, 5% decanoic acids in Dow Corning 345 fluid) to prevent engorgement of stable flies*.

| Trial No. | Pretreatment time interval | Treatment | Percent Engorgement |
|---|---|---|---|
| 1 | 0 h | C8C9C10/DC345 | 0% |
| 2 | 0 h | None (control) | 94% |
| 3 | 3 h | C8C9C10/DC345 | 0% |
| 4 | 3 h | None (control) | 52% |

*A different type of membrane was used in trials 3 and 4, which reduced the number of engorging flies for control trial 4.

The inventive insect and arthropod repellent, formulated in a volatile silicone fluid, was shown to repel and incapcitate stable flies. This finding demonstrated that repellency was not limited to mosquitoes, but extends to other biting flies, insects, or arthropods thus demonstrating the utility of the novel insect and arthropod repellent for protecting pets and livestock as well as humans.

In summary, the present invention describes a novel insect and arthropod repellent that provides long lasting protection against mosquitoes, and that is stable, commercially available, economically competitive, safe (noted GRAS by the FDA).

The description of illustrative embodiments and best modes of the present invention is not intended to limit the scope of the invention. Various modifications, alternative constructions and equivalents may be employed without departing from the true spirit and scope of the appended claims.

What is claimed is:

1. A method for repelling insects away from a human or an animal, the method comprising:
   obtaining an insect repellant composition comprising
   a) a dermatologically acceptable carrier, and
   b) active ingredients consisting essentially of
      a mixture of fatty acids, each of the fatty acids having a straight carbon chain of 6 to 12 carbon atoms long, wherein the mixture of fatty acids includes
         (i) a first fatty acid molecule having 6 to 8 carbon atoms, and a carboxylic acid group,
         (ii) a second fatty acid molecule having 8 to 9 carbon atoms, and a carboxylic acid group, and
         (iii) a third fatty acid molecule having 9 to 12 carbon atoms, and a carboxylic acid group,
      wherein the first fatty acid molecule, the second fatty acid molecule, and the third fatty acid molecule are all different, are in about a 1:1:1 ratio by weight in the active ingredients, and are in the insect repellent composition in an amount effective to repel more insects away from a test subject that has been treated with the insect repellant composition than a control subject without the insect repellant composition after about 3 hours or more; and applying the insect repellant composition to the human or the animal to repel insects.

2. The method of claim 1, wherein the active ingredients consist essentially of about 10 to 90 % by weight of the first fatty acid molecule, about 10 to 90 % by weight of the second fatty acid molecule, and about 10 to 90 % by weight of the third fatty acid molecule, wherein the weight percentages of the first, second, and third fatty acid molecules are based on the weight of the active ingredients.

3. The method of claim 1 wherein the dermatologically acceptable carrier comprises silicone.

4. The method of claim 1 wherein applying the insect repellent composition comprises applying a topical dose of the insect repellent composition to the human or the animal, wherein the topical dose includes about 0.3 mg/cm$^2$ or more of the active ingredients.

5. The method of claim 1 wherein the insects are biting stable flies.

6. The method of claim 1 wherein the animal is livestock.

7. The method of claim 1 wherein:
the first fatty acid molecule is octanoic acid,
the second fatty acid molecule is nonanoic acid, and
the third fatty acid molecule is decanoic acid.

8. The method of claim 1 wherein the active ingredients consist of the first fatty acid molecule, the second fatty acid molecule, and the third fatty acid molecule.

9. The method of claim 1 wherein applying the insect repellent composition to the human or the animal comprises applying the insect repellent composition to livestock, and wherein the method further comprises:
repelling insects away from the livestock for at least about 3 hours.

10. The method of claim 9 wherein the active ingredients consist essentially of about 10 to 90 % by weight of the first fatty acid molecule, about 10 to 90 % by weight of the second fatty acid molecule, and about 10 to 90 % by weight of the third fatty acid molecule, wherein the weight percentages of the first, second, and the third fatty acid molecules are based on the weight of the active ingredients.

11. The method of claim 1 wherein the insects are flies.

12. The method of claim 1 wherein the insects are mosquitoes.

13. A method for repelling flies or mosquitoes away from a human or an animal, the method comprising:
obtaining an insect repellant composition comprising
a) a dermatologically acceptable carrier, and
b) active ingredients comprising
(i) octanoic acid,
(ii) nonanoic acid, and
(iii) decanoic acid,
wherein the octanoic acid, nonanoic acid, and decanoic acid are in the insect repellant composition in an amount effective to repel more flies or mosquitoes away from a test subject that has been treated with the insect repellant composition than a control subject without the insect repellant composition after about 3 hours or more, and wherein the octanoic acid, the nonanoic acid, and the decanoic acid are in about a 1:1:1 ratio by weight in the active ingredients; and
applying the insect repellant composition to the human or the animal to repel flies or mosquitoes.

14. The method of claim 13 wherein applying the insect repellent composition comprises applying the insect repellent composition to the animal.

15. The method of claim 13 wherein the dermatologically acceptable carrier comprises silicone.

16. An insect repellent composition comprising:
a) a dermatologically acceptable carrier; and
b) active ingredients consisting of
a mixture of fatty acids, each of the fatty acids having a straight carbon chain 6 to 12 carbon atoms long, wherein the mixture of fatty acids is
(i) a first fatty acid molecule having 6 to 8 carbon atoms, and a
carboxylic acid group,
(ii) a second fatty acid molecule having 8 to 9 carbon atoms, and
a carboxylic acid group,
and
(iii) a third fatty acid molecule having 9 to 12 carbon atoms, and
a carboxylic acid group, and
wherein the first fatty acid molecule, the second fatty acid molecule, and the third fatty acid molecule are all different, are in about a 1:1:1 ratio by weight in the active ingredients, and are in the insect repellent composition in an amount effective to repel more insects away from a test subject with the insect repellent composition than a control subject without the insect repellant composition after about 3 hours or more.

17. The insect repellant composition of claim 16 wherein the insect repellent composition that is on the test subject has a surface concentration of the active ingredients of about 0.3 mg/cm$^2$ or more.

18. The insect repellent composition of claim 16 wherein the first fatty acid molecule is octanoic acid and the third fatty acid molecule is decanoic acid.

19. An insect repellent composition comprising:
a) a dermatologically acceptable carrier; and
b) active ingredients comprising
(i) octanoic acid,
(ii) nonanoic acid, and
(iii) decanoic acid,
wherein the octanoic acid, the nonanoic acid, and the decanoic acid are in the insect repellent composition in an amount effective to repel more flies or mosquitoes away from a test subject that has been treated with the insect repellant composition than a control subject without the insect repellant composition after about 3 hours or more, and wherein octanoic acid, nonanoic acid, and decanoic acid are in about a 1:1:1 ratio by weight in the active ingredients.

20. The insect repellent composition of claim 19 wherein octanoic acid, nonanoic acid, and decanoic acid are each in the insect repellent composition in an amount of about 10 to about 90% by weight of the active ingredients.

21. The insect repellent composition of claim 19 wherein the insect repellent composition that is on the test subject has a surface concentration of the active ingredients of about 0.3 mg/cm$^2$ or more.

22. The insect repellent composition of claim 19 wherein the active ingredients consist essentially of the octanoic acid, the nonanoic acid, and the decanoic acid.

* * * * *